United States Patent [19]
Ditter et al.

[11] Patent Number: 5,979,670
[45] Date of Patent: Nov. 9, 1999

[54] LARGE PORE SYNTHETIC POLYMER MEMBRANES

[75] Inventors: Jerome Ditter, Santa Ana; Richard A. Morris, Encinitas; Robert Zepf, San Diego, all of Calif.

[73] Assignee: USF Filtration and Separations Group Inc., Timonium, Md.

[21] Appl. No.: 08/872,347

[22] Filed: Jun. 11, 1997

Related U.S. Application Data

[60] Continuation of application No. 08/476,189, Jun. 7, 1995, abandoned, which is a division of application No. 08/206,114, Mar. 4, 1994, abandoned.

[51] Int. Cl.$^6$ .................................................. B01D 29/00
[52] U.S. Cl. ............... 210/489; 210/500.34; 210/500.38; 210/500.4; 210/500.41; 210/500.43; 422/56; 436/531
[58] Field of Search ........................ 210/500.34, 500.38, 210/500.41, 500.42, 490, 489, 500.43, 500.22; 422/56; 436/531

[56] References Cited

U.S. PATENT DOCUMENTS

| | | |
|---|---|---|
| 3,615,024 | 10/1971 | Michaels . |
| 4,125,372 | 11/1978 | Kawai et al. . |

(List continued on next page.)

FOREIGN PATENT DOCUMENTS

| | | |
|---|---|---|
| 0 036 315 A3 | 9/1981 | European Pat. Off. . |
| 0 037 730 A2 | 10/1981 | European Pat. Off. . |
| 0 247 596 A3 | 12/1987 | European Pat. Off. . |
| 0 345 781 A2 | 12/1989 | European Pat. Off. . |
| 0 407 800 A2 | 1/1991 | European Pat. Off. . |
| 0 415 679 A2 | 3/1991 | European Pat. Off. . |
| 0 473 241 A2 | 3/1992 | European Pat. Off. . |
| 0 475 692 A1 | 3/1992 | European Pat. Off. . |
| 0 479 394 A2 | 4/1992 | European Pat. Off. . |
| 0 497 334 A1 | 8/1992 | European Pat. Off. . |
| 0 503 596 A2 | 9/1992 | European Pat. Off. . |
| 0 574 134 A2 | 12/1993 | European Pat. Off. . |
| WO 91/03312 | 3/1991 | Germany . |
| 42 12 280 A1 | 10/1993 | Germany . |
| 2199786 | 7/1988 | United Kingdom . |
| 2199786 | 3/1990 | United Kingdom . |

OTHER PUBLICATIONS

Strathmann, et al., "The Formation Mechanism of Phase Inversion Membranes", *Desalination* 21:241–255 (1977).
Walhauser, "Bateria Removal Filtration with Highly Asymmetric Filter Media", *Pharma Int'l.* (1983).
R.E. Kesting, "The Four Tiers of Structure in Integrally Skinned Phase Inversion Membranes and Their Relevance to the Various Separation Regimes", *J. App. Polymer Science* 41:2739–2752 (1990).
K.C. Kock, "Untersuchungen uber den Bildungsmechanisms asymmetrischer Membranen fur umgekehrte Osmose" (1975) (original and translation).
L.T. Rozelle, Research and Development Progress Report No. 359, particularly pp. 37–43 (Oct. 1968).
R.E. Kesting, et al., "Highly anisotropic microfiltration membranes", *Pharmaceutical Technology* 5:52–60 (1981).
R.E. Kesting, "Phase Inversion Membranes", pp. 131–164 in *Materials Science of Synthetic Membranes* (Lloyd, D.R. ed., ACS, Washington, D.C. (1985)).
R.E. Kesting, et al., "Synthetic Polymeric Membranes: A Structural Perspective", Second Edition, Irvine, CA, p. 227 (1985).

*Primary Examiner*—Ana Fortuna
*Attorney, Agent, or Firm*—Knobbe, Martens, Olson & Bear, LLP

[57] ABSTRACT

Highly asymmetric polymeric membranes with large pores which yield bubble points in the range of 0.5 to 25 psid and superior flow characteristics. The membranes can be cast from both metastable dispersions and from homogenous casting formulations. The technique of synthesis involves exposure of the cast membrane to humid air to create large surface pores on the exposed side.

30 Claims, 17 Drawing Sheets

U.S. PATENT DOCUMENTS

| | | |
|---|---|---|
| 4,168,146 | 9/1979 | Grubb et al. . |
| 4,212,742 | 7/1980 | Solomon et al. . |
| 4,225,557 | 9/1980 | Hartl et al. . |
| 4,333,972 | 6/1982 | Kesting . |
| 4,387,024 | 6/1983 | Kurihara et al. . |
| 4,551,427 | 11/1985 | Draeger et al. . |
| 4,604,264 | 8/1986 | Rothe et al. . |
| 4,614,714 | 9/1986 | Kuskabe et al. . |
| 4,629,563 | 12/1986 | Wrasidlo ................. 210/500.41 X |
| 4,637,978 | 1/1987 | Dappen . |
| 4,761,233 | 8/1988 | Under et al. ................. 210/500.37 |
| 4,774,039 | 9/1988 | Wrasidlo . |
| 4,774,192 | 9/1988 | Terminiello et al. ................. 436/530 |
| 4,790,979 | 12/1988 | Terminiello et al. . |
| 4,797,256 | 1/1989 | Watlington, IV . |
| 4,814,082 | 3/1989 | Wrasidlo . |
| 4,820,489 | 4/1989 | Rothe et al. . |
| 4,871,258 | 10/1989 | Herpichboehm et al. . |
| 4,885,077 | 12/1989 | Karakelle et al. . |
| 4,897,173 | 1/1990 | Nankai et al. . |
| 4,902,422 | 2/1990 | Pinnau et al. . |
| 4,933,081 | 6/1990 | Sasaki et al. . |
| 4,935,346 | 6/1990 | Phillips et al. . |
| 4,987,085 | 1/1991 | Allen et al. . |
| 4,992,385 | 2/1991 | Godfrey . |
| 4,994,238 | 2/1991 | Daffern et al. . |
| 5,069,945 | 12/1991 | Wrasidlo . |
| 5,096,809 | 3/1992 | Chen et al. . |
| 5,171,445 | 12/1992 | Zepf . |
| 5,179,005 | 1/1993 | Phillips et al. . |
| 5,185,256 | 2/1993 | Nankai et al. . |
| 5,188,734 | 2/1993 | Zepf . |
| 5,846,422 | 12/1998 | Ditter et al. ................. 210/500.22 |

LARGE PORE SYNTHETIC POLYMER MEMBRANES

This application is a file wrapper continuation of U.S. patent application Ser. No. 08/476,189, filed Jun. 7, 1995, which was a divisional of U.S. patent application Ser. No. 08/206,114, filed Mar. 4, 1994.

BACKGROUND OF THE INVENTION

1. Field of the Invention

The invention relates to the field of microfiltration membranes; it relates particularly to microfiltration membranes composed of synthetic polymers.

2. Background of the Prior Art

Highly asymmetric polymeric membranes prepared from phase separated (inversion) casting mixes have been described in patents by Wrasidlo U.S. Pat. Nos. 4,629,563 and 4,774,039, and Zepf, U.S. Pat. Nos. 5,188,734 and 5,171,445, the disclosures of which are hereby incorporated by reference. Wrasidlo discloses highly asymmetric, integrally skinned membranes, having high flow rates and excellent retention properties, prepared from a metastable two-phase liquid dispersion of polymer in solvent/nonsolvent systems. Zepf discloses improved Wrasidlo-type polymer membranes having a substantially greater number of skin pores of more consistent size, and greatly increased flow rates, with reduced flow covariance for any given pore diameter. The improved Zepf membranes are achieved by modifications to the Wrasidlo process, comprising reduced casting and quenching temperatures, and reduced environmental exposure between casting and quenching. Zepf further teaches that reduced casting and quenching temperatures minimize the sensitivity of the membrane formation process to small changes in formulation and process parameters.

A phase inversion polymeric membrane is conventionally made by casting a solution or a mix comprising a suitably high molecular weight polymer(s), a solvent(s), and a nonsolvent(s) into a thin film, tube, or hollow fiber, and precipitating the polymer by one or more of the following mechanisms: (a) evaporation of the solvent and nonsolvent; (b) exposure to a nonsolvent vapor, such as water vapor, which absorbs on the exposed surface; (c) quenching in a nonsolvent liquid, generally water; or (d) thermally quenching a hot film so that the solubility of the polymer is suddenly greatly reduced.

The nonsolvent in the casting mix is not necessarily completely inert toward the polymer, and in fact it usually is not and is often referred to as swelling agent. In the Wrasidlo-type formulations, as discussed later, selection of both the type and the concentration of the nonsolvent is crucial in that it is the primary factor in determining whether or not the mix will exist in a phase separated condition.

In general, the nonsolvent is the primary pore forming agent, and its concentration in the mix greatly influences the pore size and pore size distribution in the final membrane. The polymer concentration also influences pore size, but not as significantly as does the nonsolvent. It does, however, affect the strength and porosity (void volume). In addition to the major components in the casting solution (mix), there can be minor ingredients, for example, surfactants or release agents.

Polysulfone is especially amenable to formation of highly asymmetric membranes, particularly in the two-phase Wrasidlo formulations. These are not homogeneous solutions but consist of two separate phases, one a solvent-rich clear solution of lower molecular weight polymer at low concentrations (e.g., 7%) and the other a polymer-rich turbid (colloidal) solution of higher molecular weight polymer at high concentrations (e.g., 17%). The two phases contain the same three ingredients, that is, polymer, solvent, and nonsolvent but in radically different concentrations and molecular weight distributions. Most importantly, the two phases are insoluble in one another and, if allowed to stand, will separate. The mix must be maintained as a dispersion, with constant agitation up until the time that it is cast as a film.

It is the nonsolvent and its concentration in the casting mix that produces phase separation, and not every nonsolvent will do this. The ones that do probably have a role similar to that of a surfactant, perhaps creating a critical micelle concentration by aligning some of the larger polymer molecules into aggregates, or colloids, which are then dispersed in the remaining non-colloidal solution. The two phases will separate from one another if allowed to stand, but each individual phase by itself is quite stable. If the temperature of the mix is changed, phase transfer occurs. Heating generates more of the clear phase; cooling does the reverse. Concentration changes have the same effect, but there is a critical concentration range, or window, in which the phase separated system can exist, as discussed by Wrasidlo. Wrasidlo defines this region of instability on a phase diagram of thus dispersed polymer/solvent/nonsolvent at constant temperature, lying between spinodal and binodal curves, wherein the polymer is not completely miscible with solvent.

Because of the great hydrophobicity of the polymer and because of the thermodynamically unstable condition of the casting mix, wherein there pre-exist two phases, one solvent-rich and the other polymer-rich (a condition that other systems must pass through when undergoing phase inversion), the unstable Wrasidlo mixes precipitate very rapidly when quenched, form a tight skin at the interface, and consequently develop into highly asymmetric membranes. Asymmetric here means a progressive change in pore size across the cross-section between skin (the fine pored side of the membrane that constitutes the air-solution interface or the quench-solution interface during casting) and sub-structure. This stands in contrast to reverse osmosis and most ultrafiltration membranes which have abrupt discontinuities between skin and substructure and are also referred to in the art as asymmetric.

Polymeric membranes can also be cast from homogeneous solutions of polymer. The composition of these formulations lie outside of the spinodal/binodal region of the phase diagram of Wrasidlo. Membranes cast from homogeneous solutions may also be asymmetric, although not usually to the same high degree of asymmetry as those cast from phase separated formulations.

Increasing the surface pore size of membranes has been described. See UK Patent No. 2,199,786 to Fuji (herein "Fuji") . The prior art teaches exposing the cast polymer solution to humid air in order to cause a phase inversion at a point below the surface of the membrane. See Fuji. The membranes produced in accordance with the Fuji process have a characteristic structure of relatively wide pores on the surface (i.e., 0.05–1.2 $\mu$m), followed by progressively constricting pore sizes to the phase inversion point below the surface, followed by an opening of the pores until an isotropic structure is achieved progressing to the cast surface (i.e., 1–10 $\mu$m). Accordingly, the Fuji membranes can be thought of as having reverse asymmetry from the skin surface to the point of inversion and asymmetry progressing into an isotropic structure. The patent expressly teaches that minimal asymmetry should be used in order to prolong the life of the membranes. See Page 4, Lines 7–29. Further, it appears as though the Fuji membranes are generally prepared with formulations having relatively high viscosities. For example, the polymer concentrations are usually quite high and in many cases, the membranes are prepared using polymers as non-solvents. See Example 2, page 12; Example 3, page 15.

Synthetic polymer membranes are useful as highly retentive, highly permeable filters in many testing applications in the food and beverage industry, and in medical laboratories. Many of these operations would be more cost effective and more commercially attractive if the filtration range of the membranes could be extended over the existing Wrasidlo and Zepf-type membranes.

SUMMARY OF THE INVENTION

In accordance with a first aspect of the present invention, there is provided a polymer membrane comprising a first surface, a second surface, and a porous supporting structure therebetween, wherein the first surface comprises a relatively open pore structure and the second surface comprises a more open pore structure and wherein the supporting structure comprises a high degree of asymmetry through at least 50% of the supporting structure but no more than 80% of the supporting structure.

In accordance with a second aspect of the present invention, there is provided a polymer membrane comprising a first porous surface, a second porous surface, and a porous supporting structure having a thickness therebetween, wherein the supporting structure has a generally isotropic structure from the first surface to a point at about one-quarter of the thickness of the supporting structure and a generally asymmetric structure from the point to the second surface.

In accordance with a third aspect of the present invention, there is provided a polymer membrane comprising a first porous surface, a second porous surface, and a supporting structure having a thickness therebetween, the supporting structure defining porous flow channels between the first and second surface, wherein the flow channels have a substantially constant mean diameter from the first surface to a point at about one-quarter of the thickness of the supporting structure and an increasing mean diameter from the point to the second surface.

In accordance with a fourth aspect of the present invention, there is provided a porous polymer membrane suitable for isolating a liquid fraction from a suspension, comprising an integral porous skin, lying at one face of the membrane, wherein substantially all of the pores of the skin have diameters greater than about 1.2 microns, and a support region of the membrane lying below the skin and having an asymmetric structure.

In accordance with a fifth aspect of the present invention, there is provided an improved asymmetric polymer membrane having a first porous surface, a second porous surface, and a porous supporting structure therebetween and having a thickness, the improvement comprising a region of generally isotropic structure from the first surface to a point at about one-quarter of the thickness of the supporting structure.

In accordance with a sixth aspect of the present invention, there is provided a method for preparing a polymer membrane having a relatively large skin pore size, a substantially asymmetric structure, and an enhanced flow rate, comprising preparing a metastable casting dispersion comprising a polymer-rich phase and a polymer-poor phase at a selected casting temperature, casting the dispersion into a thin layer at the casting temperature, contacting the cast layer with a pore forming atmosphere for a period time sufficient to form surface pores greater than 1.2 microns, quenching the cast layer with a non-solvent quench liquid in which the solvent is miscible and in which the polymer is substantially insoluble to precipitate the polymer as an integral membrane, and recovering the membrane from the quench liquid.

In accordance with a seventh aspect of the present invention, there is provided a method for preparing a polymer membrane having a relatively large skin pore size, a substantially asymmetric structure, and an enhanced flow rate, comprising preparing a homogeneous casting solution comprising a polymer, a solvent for the polymer, and a nonsolvent for the polymer at a casting temperature, casting the dispersion into a thin layer at the casting temperature, contacting the cast layer with a pore forming atmosphere for a period time sufficient to form surface pores greater than 1.2 microns, and quenching the cast layer with a non-solvent quench liquid in which the solvent is miscible and in which the polymer is substantially insoluble to precipitate the polymer as an integral membrane, recovering the membrane from the quench liquid, wherein the membrane has substantial asymmetry through at least fifty percent of the membrane.

In accordance with an eighth aspect of the present invention, there is provided an integrally skinned asymmetric polysulfone membrane, having a surface pore mean diameter of at least about 1.2 microns, prepared by the foregoing methods.

In accordance with a ninth aspect of the present invention, there is provided an improved process to prepare an integrally skinned highly asymmetric polymer membrane, the improvement comprising contacting the cast layer with a gaseous atmosphere with a pore forming atmosphere for a period time sufficient to form surface pores greater than 1.2 microns.

In accordance with a tenth aspect of the present invention, there is provided an improved diagnostic device comprising a filtering means that delivers a filtrate that is substantially particle free containing an analyte to an analyte-detecting region of the device, the improvement comprising a filtering means comprising one of the foregoing polymer membranes having surface pores of a mean diameter of from greater than about 1.2 microns and having a flow rate of greater than about 4.5 cm/min/psi.

In accordance with an eleventh aspect of the present invention, there is provided an improved diagnostic device comprising a lateral wicking means that transfers a sample that is substantially particle free containing an analyte from a sample receiving region of the device to an analyte-detecting region of the device, the improvement comprising a lateral wicking means comprising one of the foregoing polymer membranes having surface pores of a mean diameter of from about 1.2 microns and having a lateral transfer rate of greater than about 2 cm per minute.

In accordance with a twelfth aspect of the present invention, there is provided a filter unit, comprising one of the foregoing polymer membranes.

In preferred embodiments of the invention, the polymer is a polysulfone. Preferably, the bubble points of the membranes of the invention or the membranes produced or used in accordance with the invention are not greater than about 25 psid and are preferably from about 0.5 psid to about 25 psid, even more preferably, the bubble point is from about 5 psid to about 15 psid. Also, preferably, the membranes of the invention or the membranes produced or used in accordance with the invention have a mean aqueous flow rate of from about 4.5 to 25 cm/min psid.

BRIEF DESCRIPTION OF THE DRAWINGS

FIG. 1a is a skin surface view of the membrane. FIG. 1b is a cast surface view of the membrane. FIG. 1c is a cross-sectional view of the membrane.

FIG. 2a is a skin surface view of the membrane. FIG. 2b is a cast surface view of the membrane. FIG. 2c is a cross-sectional view of the membrane.

FIG. 3a is a skin surface view of the membrane. FIG. 3b is a cast surface view of the membrane. FIG. 3c is a cross-sectional view of the membrane.

FIG. 4a is a skin surface view of the membrane. FIG. 4b is a cast surface view of the membrane. FIG. 4c is a cross-sectional view of the membrane.

FIG. 5a is a skin surface view of the membrane. FIG. 5b is a cast surface view of the membrane. FIG. 5c is a cross-sectional view of the membrane.

DETAILED DESCRIPTION OF THE INVENTION

Figure 1A:
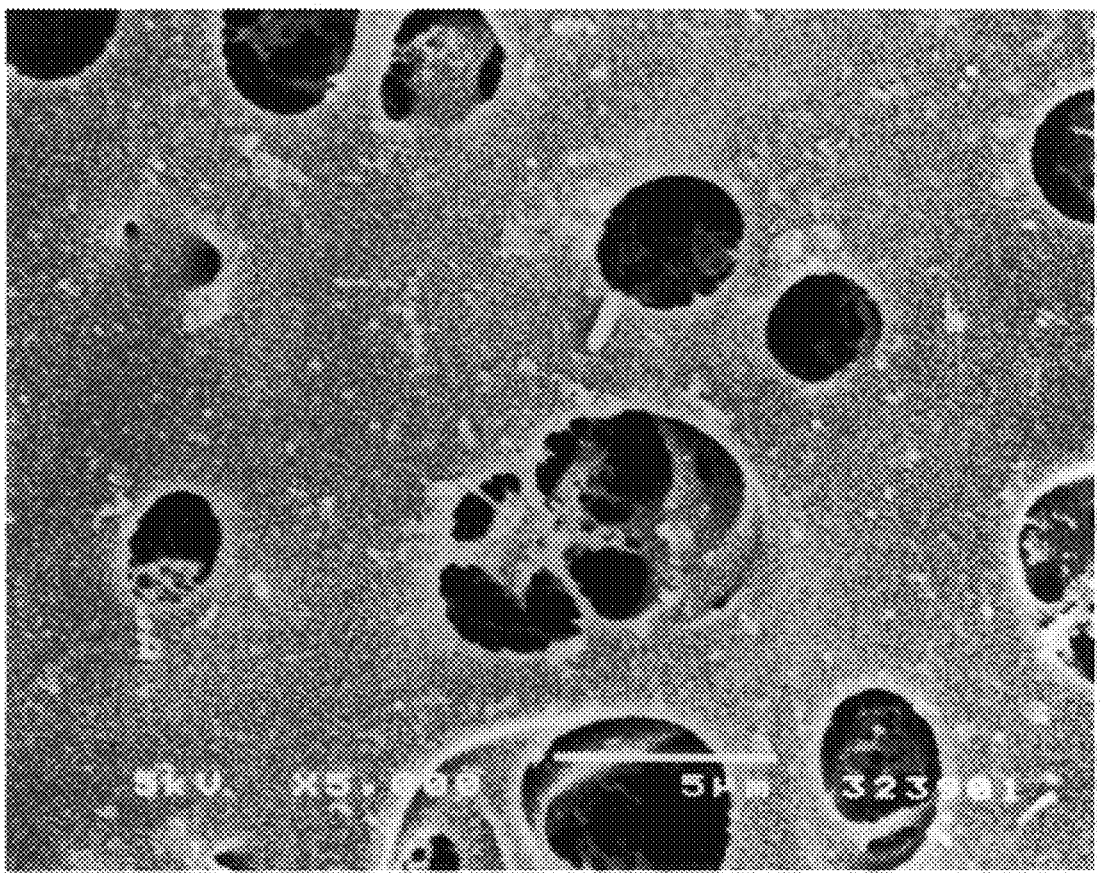
FIGS. 1a, 1b, 1c are a series of scanning electron microscope images of an open pored membrane prepared in accordance with the invention from a polysulfone polymer dispersion (Wrasidlo-type) that has a bubble point of 8 psid.

The invention provides improved asymmetric polysulfone membranes with large pores having improved flow rates and wicking performance while retaining good separation capabilities. Pore size, and indirectly flow rate, is conveniently measured by bubble point, which is the minimum pressure required to push a bubble of air through a wetted membrane. Zepf-type polymeric membranes typically have bubble points greater than 25 psid. The membranes of the invention, by comparison, have bubble points less than about 25 psid, in the range 0.5 to 25 psid and preferably 2 to 20 psid or more preferably 5 to 15 psid.

Moreover, the membranes of the invention have relatively large skin pores in comparison to Wrasidlo and Zepf membranes. For example, the average skin pore sizes of membranes of the invention generally exceed 1.2 $\mu$m and more generally are 2–3 $\mu$m or even larger. In contrast, the Wrasidlo and Zepf membranes have average skin pore sizes less than 1.2 $\mu$m and usually less than 0.35 $\mu$m.

Further, in contrast to the classical asymmetric structure of Wrasidlo and Zepf, the membranes of the invention generally include asymmetry through no more than 80% of the membrane. In preferred embodiments, in the remaining at least 20% of the membrane, the membrane exhibits a generally isotropic region.

The improved membranes of the invention have been found to provide important advantages in filtration applications. For example, the membranes of the invention are useful in conventional filtration applications, such as those used in beer and wine filtration and water treatment applications. In addition, the membranes of the invention are useful in diagnostic or biological applications, such as in the manufacture of biosensors.

The membranes of the invention can be prepared from homogeneous casting solutions as well as from the phase separated mixes as delineated in the Wrasidlo '563 and '039 and in the Zepf '734 and '445 patents.

Generally, in the manufacture of the membranes of the invention, the cast film is exposed to air in order to create large surface pores on the exposed side, followed by standard nonsolvent quenching (i.e., in water). The diameter of the surface pores can be varied through the length of the exposure time as well as through the humidity of the air. In exposure to the air, any water vapor in the air acts to precipitate the polymer at and in a region below the exposed liquid film surface. Unexpectedly, what is observed is that a region forms on and below the surface in which a generally isotropic structure having relatively large pore sizes is formed. Below this area, classical asymmetry is observed. In general, the greater the humidity the larger the surface pores, and conversely the lower the humidity the tighter the surface.

Architecture of the Open Pore Membranes of the Invention

The polymer membranes of the invention retain a substantial degree of asymmetry while having relatively large skin pores. A convenient method for assessing the asymmetry and pore size is the scanning electron microscope (SEM). FIGS. 1 through 3 show the cross sections, skin surface and lower surface of membrane prepared according to the invention, and the features of those aspects can be compared to those of a conventional Wrasidlo-type fine pore membrane shown in FIG. 5.

In addition to the asymmetry of the membranes and the open pore structures, the membranes of the invention are unique in the presence of an isotropic region that extends from the skin surface to a point within the substructure of the membrane. Typically, this isotropic region extends through at least 20% of the membrane thickness.

In the absence of SEM data, asymmetry can be grossly estimated as described by Kesting, *Synthetic Polymer Membranes: A Structural Perspective*, p. 275 (John Wiley & Sons, 2d edition (1985)), by applying a small dot of ink or dye to the tight face of a membrane and allowing the dye to penetrate the membrane as well as spread on its surface. The ratio of the areas coated with dye gives a rough indication of asymmetry, or the degree thereof. Pore size can also be estimated by porometry analysis and by separate measurement of the bubble point, with a higher bubble point indicating tighter pores. In a classical asymmetric membrane, it is the surface pores that are the tightest. In the membranes of the present invention, the tightest pores lie somewhere between the skin and the asymmetric region.

Porometry consists of utilizing gradually increasing pressures on a wet membrane and comparing gas flow rates with those of the dry membrane which yields data on pore sizes as well as the bubble point. For these analyses, a Coulter Porometer Model 0204 was used.

As mentioned, the membranes of the present invention include a region that is generally isotropic and a region that is substantially asymmetric. Generally isotropic (or the isotropic region), as used herein, means a region of generally constant pore size, as viewed by SEM from the skin down through a portion of the supporting structure. The isotropic region may, alternatively, be viewed as a region having flow channels of a substantially constant mean diameter. In general, the average skin pore size or diameter of the skin pores of the membranes of the invention are greater than 1.2 $\mu$m. In the isotropic region, this skin pore size generally defines the mean pore size throughout the isotropic region. For example, in preferred membranes, SEM's suggest that a membrane having a mean skin pore size of 2 $\mu$m has a average pore size of 2 $\mu$m or greater throughout the isotropic region. Similar structures are seen in membranes having 3 $\mu$m, 4 $\mu$m, 5 $\mu$m, and etc. skin pore sizes. However, it will be appreciated that the isotropic region comprises a distribution of pore sizes that visually appear isotropic. It is expected that the actual pore sizes in the isotropic region vary (as is the case with any membrane).

Typically, the isotropic region extends from the skin of the membranes into the supporting substructure through greater than about 15% of the thickness of the membrane. More preferably, the isotropic region extends through greater than 20%, 25%, or even 30% or more of the thickness of the membrane. In highly preferred embodiments, the isotropic region extends greater than about 25% the thickness of the membrane. For example, in a 125 $\mu$m membrane the isotropic region extends greater than about 25 $\mu$m from the skin into the supporting substructure.

Substantially asymmetric or anisotropic (herein, the asymmetric region), as used herein, means a degree of asymmetry similar to that disclosed in, and possessed by, membranes prepared in accordance with Wrasidlo and Zepf. In that regard, the membranes of the present invention have average skin pore sizes of greater than about 1.2 $\mu$m, while on the reverse side, the side adjacent to the support paper or belt during casting, SEM's show that the average pore sizes are at least greater than twice the average skin pore size. Thus, the ratio of skin pore size to cast surface pore size is greater than about 2:1, and in highly preferred embodiments is 3:1, 4:1, 5:1, or even 6:1 or greater. Moreover, the asymmetry is a continuous gradient only within the asymmetric region.

It should be noted that the ratio of asymmetry mentioned above is only with respect to the asymmetry measured at the surfaces. In fact the asymmetry of the membranes of the invention is much greater when the mean pore size in the asymmetric region, above the cast surface, are viewed on cross-section in scanning electron microscopy. See, for example, FIGS. 1c, 2c, and 3c. When this is done, the asymmetry of the membranes of the invention appears to be. greater than about 10:1 or 20:1 or perhaps as high as 100:1 or even 200:1.

It will also be noticed by looking through the skin pores that the pore sizes in the isotropic region are slightly larger than the pores in the skin. This fact, in combination with the observed asymmetry based on surface-surface analysis versus cross-sectional analysis indicates that "skinning" occurs on both surfaces. Without wishing to be bound by any particular theory or mode of operation, there are three plausible explanations for the skinning seen in the membranes of the invention. First, when the cast film is exposed to air, the water vapor begins to gel the film and form the incipient membrane in the top region. However, not all of the polymer may be gelled in this brief time. Therefore, when the film hits the quench liquid, the remaining unprecipitated polymer then forms a skin. Second, or alternatively, a perhaps better explanation is simply that surface contraction shrinks the pores due to the inherent difference in surface energies (somewhat analogous to a water droplet or a soap bubble that minimizes its surface-to-volume ratio). Or, third, there may be a slight migration of polymer to the surface due to the steep gradient in chemical potential.

Additionally, due to the fact that the bubble point of the membranes of the invention are generally higher than what would be predicted for the pore sizes seen in the isotropic region or in the skin, it is apparent that there must be some constriction in pore size between the isotropic region and the asymmetric region. Surprisingly, conventional reasoning would suggest that the pores below the skin should be smaller than the skin pores. In fact, they should grow progressively smaller with depth, i.e., "reverse asymmetry". Diffusion is a slow process. Thus, the pores created or formed below the skin should see less water vapor and, therefore, be smaller.

The Fuli membranes appear to confirm this conventional reasoning and have "reverse asymmetry" from the skin to an inversion point a short depth into the membrane. In contrast, the pores below the skin in the membranes of the invention appear to be of the same size or larger than the pores in the skin and remain with such isotropic or homogeneous pore distribution throughout the region.

Therefore, it appears that the isotropic region of the membranes of the invention is created by or is at least initiated by a "dry process" interaction between the water vapor in the air and the polymer film, which causes homogeneous or isotropic formation. This is analogous to cellulose mixed esters or cellulose nitrate membranes. However, it appears as though there is negligible evaporation of solvent or non-solvent, so that, when quenched, the quench liquid rushes in and fixes the isotropic region and creates and fixes the asymmetric region.

With respect to the possible constriction of the pore size distribution between the isotropic region and the asymmetric region, discussed above, which would assist in explaining the tighter pores observed in porometry analyses (i.e., 1.0 $\mu$m maximum and 0.8 $\mu$m mean pore size), there may be a process of internal "skinning" akin to the skin formation in Wrasidlo and Zepf membranes. Support for this possibility is given by Michaels in U.S. Pat. No. 3,615,024, Col. 5, lines 43–54, where it is disclosed that a gradient pore structure occurs when water permeation into a cast film is restricted by a tightened skin, which is formed by the water in the first instance. Or, alternatively, as discussed above, it is possible that while the membranes in the isotropic region appear to be isotropic on visual inspection, actually have a pore distribution that accounts for the porometry data and higher bubble point than one might anticipate in view of the large pore sizes.

Accordingly, the structure of the membranes of the present invention is distinct from classic asymmetry in that the membranes of the invention are substantially nonasymmetric (i.e., are isotropic) from the skin to a point below the surface, defined herein as the isotropic region, discussed above. Accordingly, the asymmetric region of the membrane occurs in less than about 75% of the thickness of the membrane. Whereas, in conventional or classic asymmetry, for example, in Wrasidlo and Zepf membranes, the asymmetric region occurs throughout the entire, or substantially the entire, membrane thickness. In the Fuji membranes, in contrast, the region below the skin has inverse or reverse asymmetry, and below that, has slight conventional asymmetry. It is expected that the probable higher viscosities of the Fuji casting formulations contributes to this structure.

Therefore, colloquially speaking, the membranes of the invention can be viewed as having a funnel structure in terms of the flow channel configuration throughout the thickness of the membranes. For example, the pores meeting liquids flowing into the membrane from the surface that was unexposed during casting is very large. This is the asymmetric region, which would correspond to the conical portion of a funnel. As the liquid flows through the membrane, the pore sizes or flow channels gradually constrict, until, finally, the liquid enters the generally isotropic region which contains pore sizes or flow channels of substantially constant diameter, then flows out through the skin, the isotropic region corresponding to the spout of the funnel.

Figure 1B:
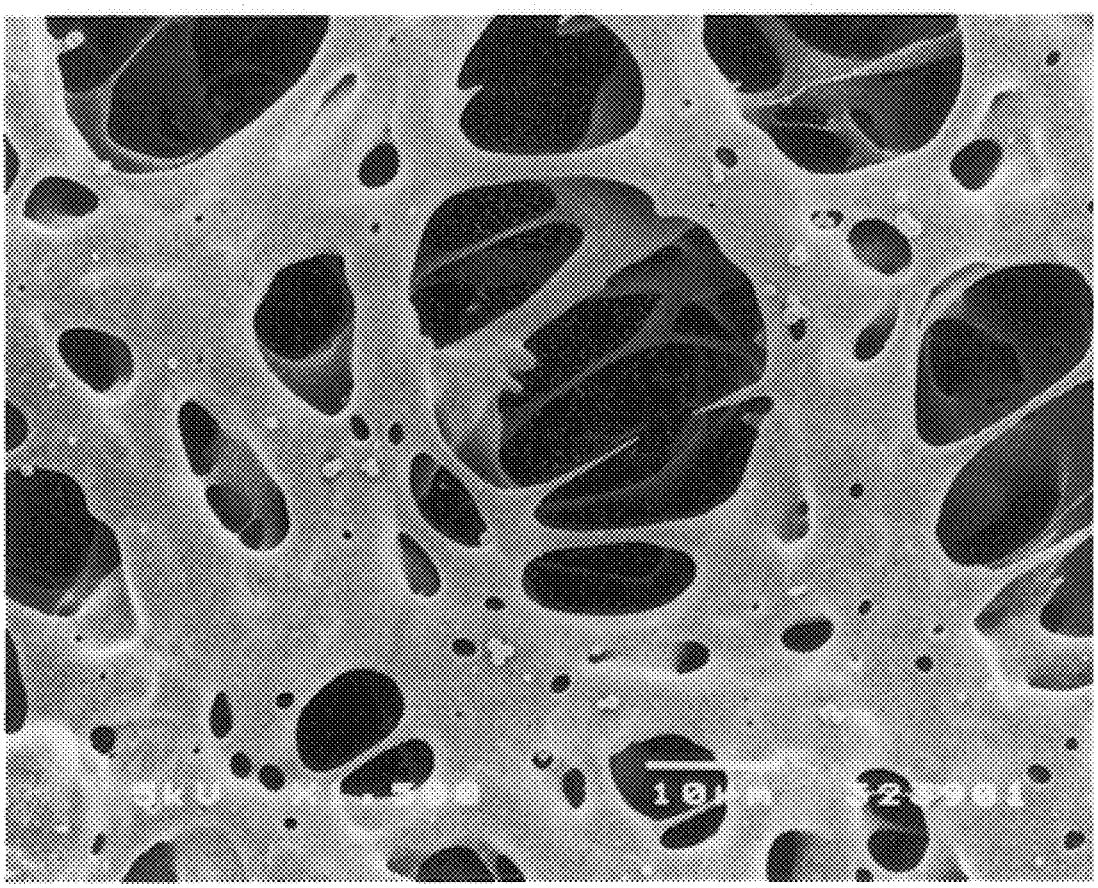
Figure 1C:
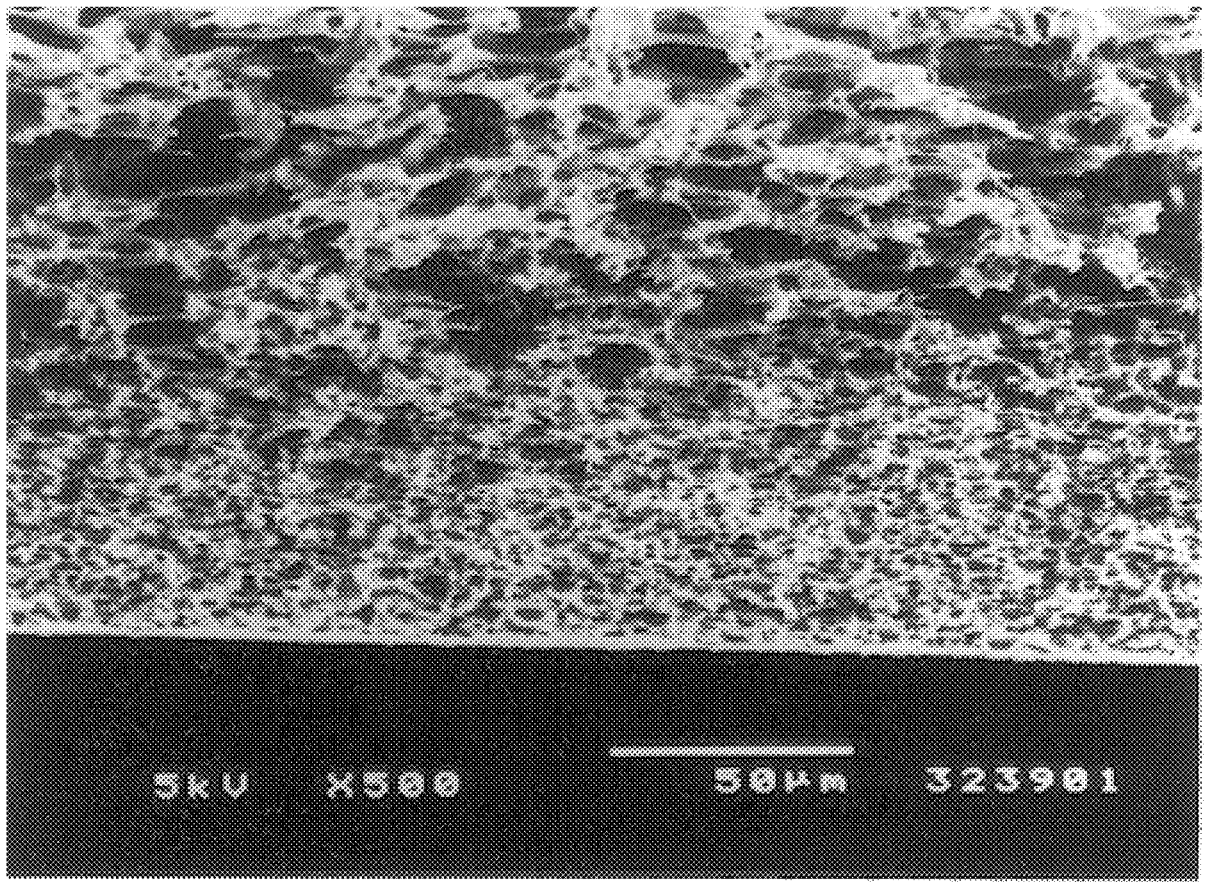

The structure of a typical open pored membrane of the invention prepared from a Wrasidlo-type dispersion is shown in FIGS. 1 through 3. The membrane has skin surface pores of, on average, 3 $\mu$m (FIG. 1a), cast surface pore sizes of, on average, 20 $\mu$m (FIG. 1b), and, in cross-section, demonstrate an isotropic region including pores sizes around 3 $\mu$m extending from the skin through approximately 25% of the thickness of the membrane, followed by an asymmetric region that opens from pore sizes of approximately 3 $\mu$m to about 20 $\mu$m from the end of the isotropic region to the cast surface (FIG. 1c). As will be appreciated, the degree of asymmetry based on these observations is approximately 6:1. The particular membrane of the Figure has a bubble point of 8 psid. The membranes shown in FIGS. 2 and 3 have very similar structures but possess bubble points of 11 and 16 psid, respectively.

Figure 4A:
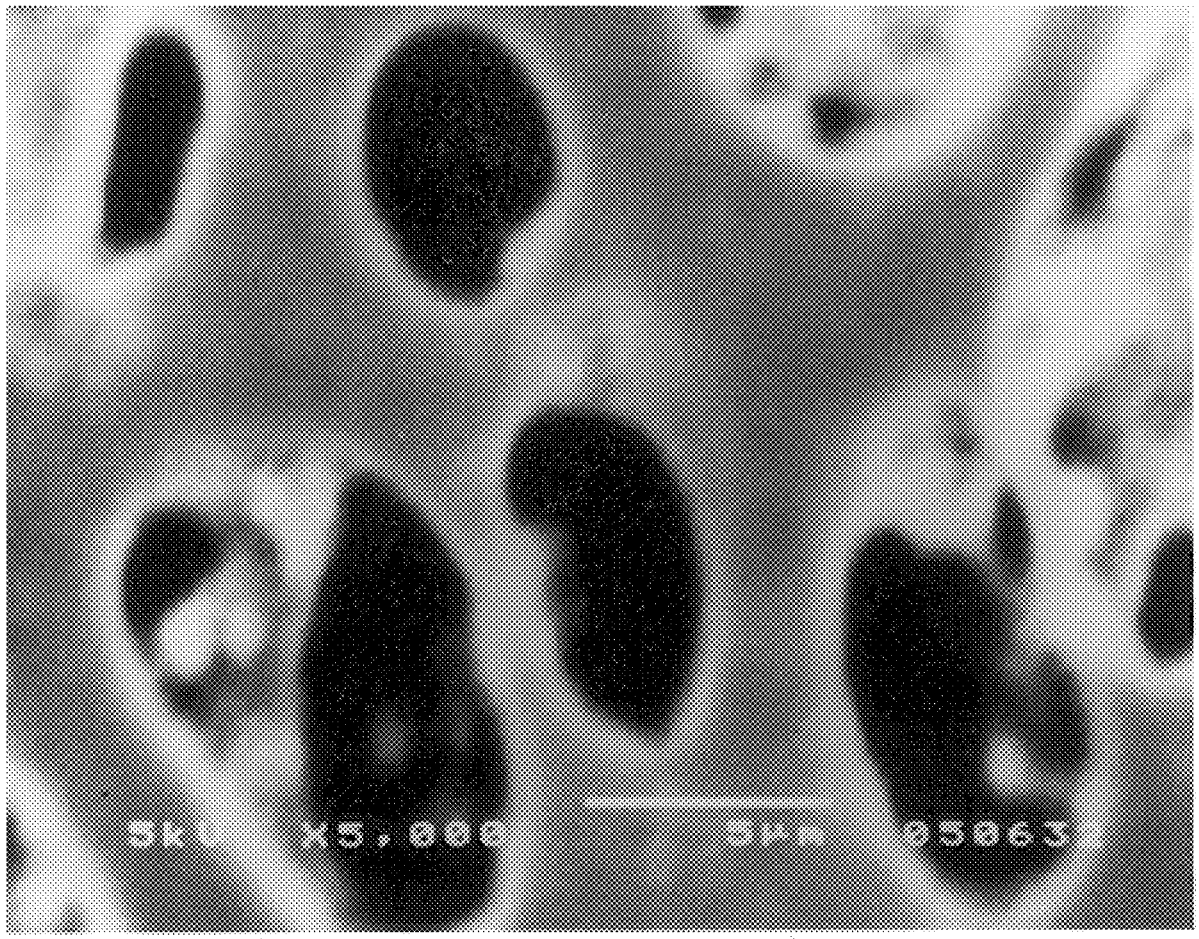
FIGS. 4a, 4b, 4c are a series of scanning electron microscope images of a membrane prepared in accordance with the invention from a homogeneous polysulfone formulation.
Figure 4B:
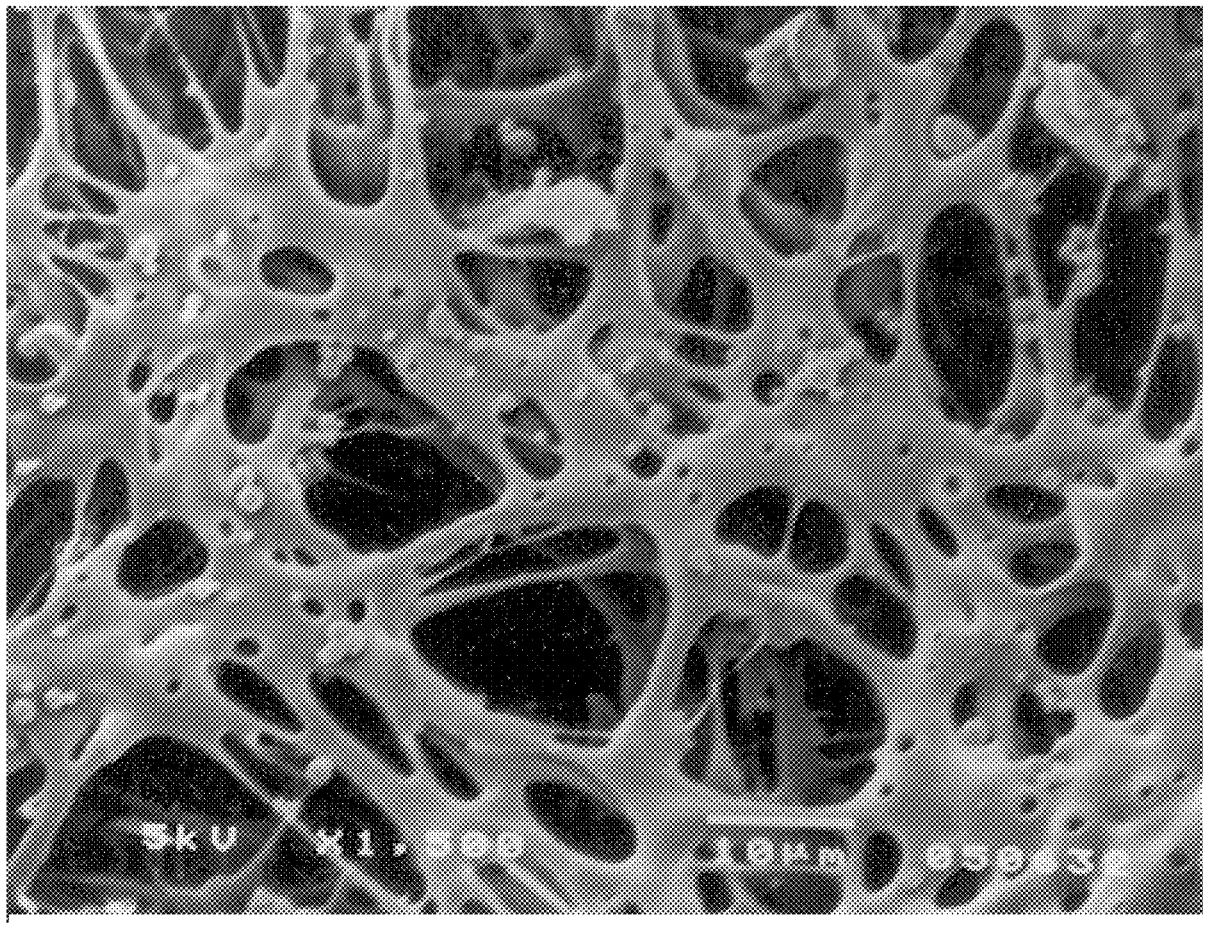
Figure 4C:
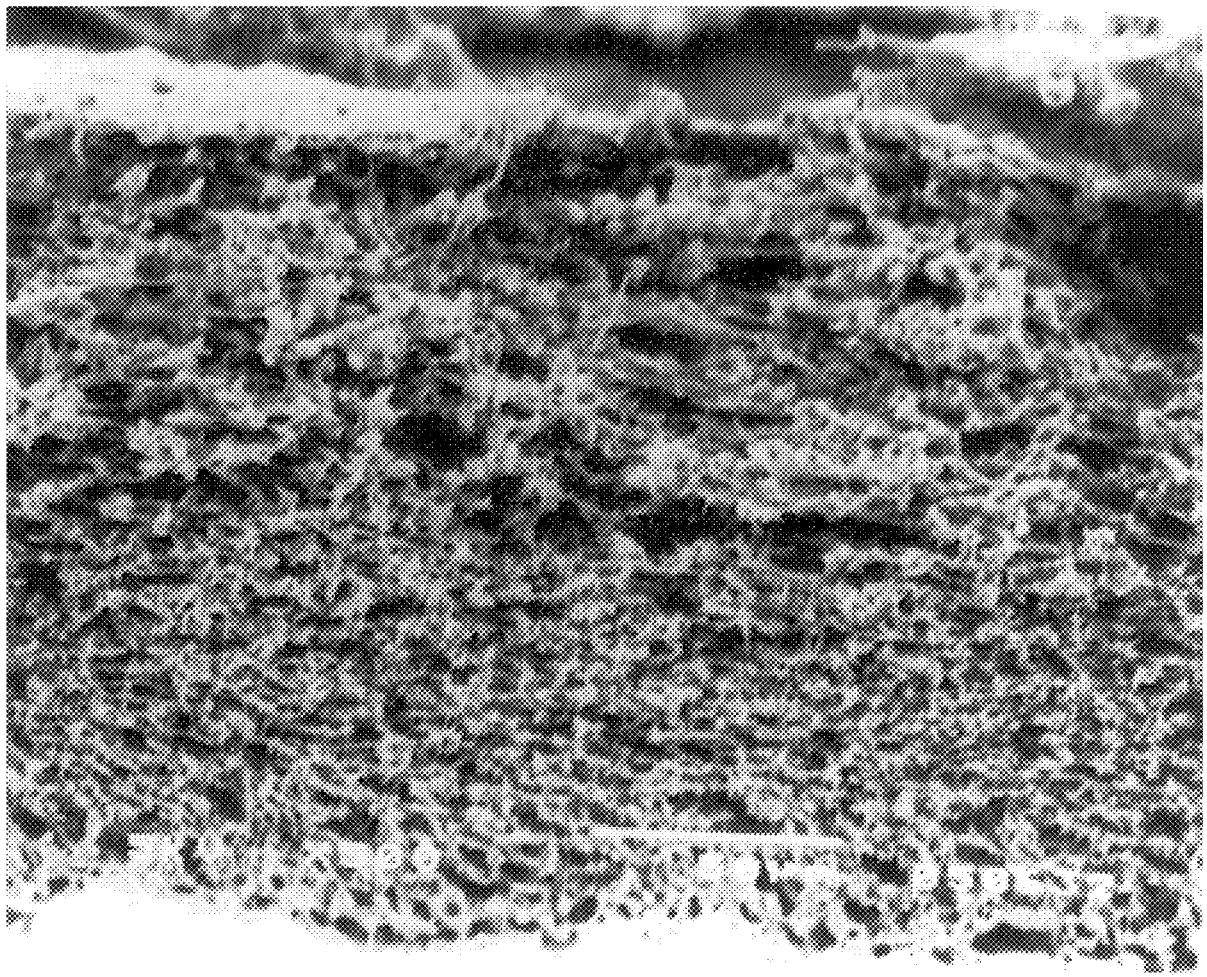

Membranes of the invention can also be prepared from homogeneous solutions. Such membranes can be prepared with bubble points in the same general range as those made from Wrasidlo mixes, but they tend to require longer periods of exposure to the air and do not possess quite the degree of asymmetry as those made from Wrasidlo-type formulations. FIG. 4 shows the structure as seen in scanning electron microscopy of a membrane produced from a homogeneous polysulfone solution, including skin surface (FIG. 4a), casting surface (FIG. 4b), and a cross-section of the membrane (FIG. 4c). This particular membrane has a bubble point of 12 psid.

In operation of the method of manufacture with Wrasidlo-type formulations, the water vapor acts on the exposed surface of the cast film to create fairly large pores both on the surface and in a region extending below the surface, while the subsequent water quench transforms the rest of the film into a highly asymmetric substructure. Because the film may be exposed to the humid air for periods of a second or more in these syntheses, it is prudent, though not necessary, to select a Wrasidlo mix that is reasonably stable with respect to phase separation, for example, formulations that under the conventional casting procedure produce asymmetric membranes of 0.45 $\mu$m or 0.2 $\mu$m pore size or smaller.

Exemplary membranes are formed using a polysulfone polymer in selected solvent/non-solvent systems; however, the polymers from which membranes of the invention can be cast are innumerable and, therefore, the suggested formulations are provided as exemplary only.

Formulations

The casting formulations for these membranes are made up of a polymer, a solvent, and a non-solvent. The polymers which can be used include any polymer capable of forming a membrane. Polymers which have been found to be particularly useful in the methods of the invention include polysulfones, polyamides, polyvinylidene halides, including polyvinylidene fluoride, polycarbonates, polyacrylonitriles, including polyalkylacrylonitriles, and polystyrene. Mixtures of polymers can be used. Preferr polysmers include Lexan polycarbonate, AMOCO P-3500 polyarylsulfone, Nylon 6/T polyhexamethylene terepthalamide, and polyvinylidine fluoride. A particularly preferred polymer is AMOCO P-3500 polyarylsulfone.

Preferred solvents which can be used in the formulations of the invention include dipolar aprotic solvents such as dimethylformamide, dimethylacetamide, dioxane, N-methyl pyrrolidone, dimethylsulfoxide, chloroform, tetramethylurea, or tetrachloroethane. Other polymer/solvent pairs are disclosed, for example, in U.S. Pat. No. 3,615,024 to Michaels.

Suitable nonsolvents include alcohols, for example, methanol, ethanol, isopropanol, amyl alcohols, hexanols, heptanols, and octanols; alkanes such as hexane, propane, nitropropane, heptane, and octane; and ketone, ethers and esters such as acetone, butyl ether, ethyl acetate, and amyl acetate.

Formulations for Wrasidlo type membranes are prepared according the methods set forth in Zepf, which is hereby incorporated by reference. In general, polymer is dissolved in solvent at the casting temperature, and the amount of nonsolvent is controlled to achieve the desired turbidity of the formulation to the desired optical density as taught by Zepf.

Homogenous casting formulations can have the composition lying outside the spinodal/binodal region of the phase diagram. Useful homogeneous formulations are any mixture that contains at least sufficient concentration of polymer to give the membrane sufficient integrity and mechanical strength and not in excess of the concentration at which the mixture becomes too viscous to cast. Usually homogeneous casting formulations comprise from about 7 to 28% polymer or mixtures of polymers and from 0 to 30% nonsolvent (w/v), the balance being solvent. The solvent and nonsolvent can also be mixtures.

In the liquid quench systems, the liquid should be chemically inert with respect to the polymer and preferably miscible with the solvent in the casting solution. The preferred quench liquid is water.

The membrane as cast is hydrophobic. However, as will be appreciated, a surfactant or wetting agent may be added to either the formulation, the quench liquid, or the rinse liquid to increase the hydrophilicity of the membrane. Preferred agents are polyhydroxycellulose, sodium dodecylsulfate, ethoxylated alcohols, glyceryl ethers, and non-ionic fluorocarbon surfactants, for example, those of the Zonyl™ type (DuPont). The concentration of surfactant in solution is not critical, and may range from a fraction of a percent (w/v) to over 10 percent.

Membrane Casting Process

The membranes of the invention can be cast using any conventional procedure wherein the casting dispersion or solution is spread in a layer onto a nonporous support from which the membrane can be later separated after quenching. The membranes can be cast either manually (i.e., poured, cast, or spread by hand onto a casting surface and quench liquid applied onto the surface) or automatically (i.e, poured or otherwise cast onto a moving bed). A preferred support is polyethylene coated paper. In casting, particularly in automatic casting, mechanical spreaders can be used. Mechanical spreaders comprise spreading knives, a "doctor blade," or spray/pressurized systems. A preferred spreading device is an extrusion die or slot coater, which comprises a chamber into which the casting formulation can be introduced and forced out under pressure through a narrow slot. In Examples 1 to 3, membranes were cast by means of a doctor blade with a knife gap of typically about 250 to 450 microns, often about 300 microns. After the quenching step, the microporous membrane product is typically about 105 to 145 microns thick.

Following casting, the dispersion is quenched. In a preferred embodiment, quenching is accomplished by moving the cast membrane on a moving bed into the quenching liquid, i.e., as a bath. The quenching liquid is most commonly of water, the temperature of which is frequently at or near the casting temperature. In the bath, the quench operation precipitates the polymer and can produce a "skin" having the requisite pore sizes and a support region having the characteristic structure. The resulting membrane is ordinarily washed free of entrained solvent and may be dried to expel additional increments of solvent, diluent, and quench liquid, and thus recover the membrane.

Generally, in preparing the membranes of the invention, the cast film should be exposed to air for a time sufficiently long enough to induce the formation of large surface pores, as discussed previously. The shorter the exposure, the higher the humidity must be, and vice versa. The total humidity is the important factor. At higher ambient air temperatures, the relative humidity can be lower for the same effect. The temperatures of the casting mix and the quench bath are also important parameters. In general, the warmer the mix, the tighter the membrane, while the warmer the quench, the more open will be the membrane.

Large Open Pore Membrane from a Wrasidlo Type Formulation

An initial attempt was made to produce a membrane having more open pores than the 0.45 μm polysulfone membrane (BTS-25) described in the Zepf patent by modifying the phase inversion formulation according to the membrane formation theory set forth in the Wrasidlo and Zepf patents, that is, increasing the optical density of the casting formulation by decreasing the polymer concentration and increasing the nonsolvent concentration, and also increasing the quench temperatures. The cast film was also exposed to humid air briefly before quenching.

It was expected that a casting formulation having an optical density in the range of 1.800 as compared to 0.600 would probably form a membrane more open than available asymmetric membranes. Indeed, the membrane produced was quite open. Permeability testing showed that the membrane had a bubble point of 4 psid, water flow rate of 17.7 cm/min-psid, and a mean flow pore size of 2.0 μm.

A more highly preferred membrane was formed by using a dispersed phase Wrasidlo type phase inversion formulation of the standard 0.2 micron polysulfone membrane (BTS 45) type and casting at lower temperature as taught by Zepf, Example 2. The low casting index of 0.176 indicates a relatively stable casting dispersion. The cast film was exposed briefly to humid air before quenching. The cast membrane was comparable in quality to the standard product, having a highly asymmetric substructure, but also having a bubble point of 8 psid and a water flow rate of 19.9 cm/min-psid. Porometry analysis indicated a mean flow pore size of 0.9 μm rather than the 0.2 μm pore diameter type and 45 psid bubble point that would have been obtained from the standard BTS-45 formulation if cast in the usual manner. Scanning electron microscope photographs (FIG. 1) showed a highly asymmetric structure, free of any large macrovoids.

Large Open Pore Membrane from a Homogenous Formulation

Example 8 demonstrates the preparation of membranes with open surface pores and a high flow rate by exposing a film cast from a homogeneous solution to humid air prior to quenching it in water. When cast with minimal exposure to humid air, the homogeneous solution, comprising 9% polysulfone in 72% solvent and 19% nonsolvent generates highly asymmetric membranes, 0.2 μm or tighter, with bubble points greater than 45 psid. Under the humid air exposure described in the example, membranes having an average bubble point of about 12 psid, and a water flow rate of 8.4 cm/min-psid were produced.

Example 9 describes the preparation of membranes from various homogeneous formulations and varying times of exposure to humid air. Independent of formulation, increased time of environmental exposure produced membranes having larger surface pores, up to 8 microns, on the tight side, and water flow rates up to greater than 19 cm/min-psid, with corresponding bubble points of 3 to 4 psid. These membranes were reasonably asymmetric, having pores on the open side of over 100 microns. See Annex I.

The initial experiments used 2-methoxyethanol as a nonsolvent; however, polyethylene glycol (PEG 400) and polyvinylpyrrolidone (PVP 10,000) also were successfully substituted in concentrations up to 256 of the total nonsolvent concentration. It is interesting to note that PVP-10,000 also acted as a good co-solvent in this situation.

In the experiments, air temperature and humidity were measured about twelve inches (30.48 cm.) above the casting plate. Air flow velocities, where recorded, were measured with a Pitot tube about one inch (2.54 cm.) above the casting plate, prior to casting.

A good example of the effects of humidity can be seen by comparing experiments 1 and 2 in Annex I. In the first experiment, stagnant air was present and in the second experiment, under otherwise comparable conditions, the air was moving. The bubble point in the membrane was halved, and the water flow rate increased by a factor of 1.7. As will be appreciated, low humidity exposures result in membranes with consequent low permeabilities and high bubble points, while higher humidity (i.e., 60%) and blowing air, the membranes had significantly reduced bubble points (i.e., 4-psid) and correspondingly high water flow rates (of up to 20.6 cm/min-psid).

The movement of humid air across the surface of the cast film increases the pore size; however, excessive air flow can disturb the liquid film in its formative stages and create distortions in the product. Therefore, we believe that the air flow should be high enough to renew continually the humid air but not so rapid as to distort the surface, preferably at a speed just slightly faster than the casting speed.

The homogeneous formulations are advantageous from the standpoint that they have greater stability than the Wrasidlo type phase separation formulations, but the latter formulations provide membranes that appear to have greater asymmetry.

Applications of the Open Pore Membranes of the Invention

The open pore polymeric membranes of the invention can improve the performance of many types of analytical devices, in particular, those devices designed to detect and measure various analytes directly in a single application step from a heterogenous fluid sample. The particular suitability of highly asymmetric open membranes for diagnostics arises from:

(a) the graded pore (asymmetric) structure with enormous size pores on the open side;

(b) increasingly smaller (but still very large) internal pores;
(c) the isotropic region below the skin; and
(d) large open pores on the "skin" side, large at least in comparison with other membranes.

These features create superb wicking tendencies, both laterally and vertically, with a liquid front travelling through these membranes at 3 to 4 times the rate of travel in the comparable tight pore membranes. At the same time they provide filtration capability. In analyses of blood samples, for example, the plasma from a blood drop quickly wicks through to the skin while the red cells are restrained by the membrane's network of filter cells. Plasma can be recovered from the skin side and analyzed in a separate layer below the membrane. With appropriate chemical reagents and enzymes imbedded in the membrane, the plasma can be rapidly analyzed for its various ingredients by colorimetry or coulometry, for example. Also, by fixing specific antibodies to the membrane, various analytes can be bound and measured. Nonspecific binding to the membrane is eliminated by preliminary treatment of the membrane with a solution of biologically inert material, such as human or bovine serum albumin, as is known to those skilled in the art. Accurate analysis requires the absence of nonspecific binding of soluble components of the fluid sample to the membrane. A hydrophilic membrane coated with surfactants has low non-specific binding properties; however, a hydrophobic membrane can be used in test devices and blocked in the conventional manner to give low non-specific binding. The handling capabilities, and lateral/vertical wicking properties are the same with hydrophobic membranes. Efficient performance of the analysis procedure depends on rapid filtration or transport of the separated fluid samples.

Membranes composed of cellulose nitrate, cellulose acetate, and mixtures thereof and occasionally their polymer blends are typically used for the porous membrane layers of such analytical devices. These membrane materials can be unsatisfactory in mechanical strength, often subject to cracking on handling, storage, and particularly in automated manufacturing processes. Nylon materials exhibit significant nonspecific binding due to the numerous active sites on the polyamide surface of the material.

The substitution of the open pore polymeric membranes of the invention for cellulose nitrate, nylon, or less open polymeric membranes in the devices described can improve both the efficiency and accuracy of the specific analytical procedure to which the device is directed. Conventional devices can be easily adapted for use with the membranes of the invention. Some of the broad applications include:

Vertical Filter Device

One class of analytical devices contains a porous membrane that delivers a filtrate either to the membrane underside or to a reaction site lying below. Chromogenic reagents for detecting analytes can be incorporated in the membrane and the colored product in the filtrate is visualized from below. See, for example, U.S. Pat. No. 4,774,192 to Terminello, the disclosure of which is hereby incorporated by reference, where chemical test systems for glucose, urea, alpha-amylase, bilirubin, triglycerides, total is cholesterol, and creatinine are described, as well as test strip immunoassays comprising enzyme labelled immunoconjugates are disclosed.

Other examples of devices of this type include U.S. Pat. No. 4,987,085 to Allen et al. for a blood filtering and metering device and U.S. Pat. No. 4,935,346 to Phillips et al. which includes a porous membrane impregnated with analyte-specific reagents to simultaneously separate a soluble filtrate from a whole blood sample applied to the upper surface of the membrane and to generate a colored reaction product which indicates the concentration of the analyte. The disclosures of such patents are incorporated by reference herein.

The membranes of the invention possess the necessary inherent properties required for performing the functions of the chemistry system as to physical characteristics, chemical inertness, and optical properties.

Lateral Wicking Device

Lateral wicking devices operate based on the capillarity or wicking properties of a substrate, such as a membrane. See, for example, U.S. Pat. No. 4,168,146 to Grubb et al. which discloses a diagnostic device for immunological quantitation having a porous carrier material to which antibodies are covalently bound, the disclosure of which is incorporated by reference.

The efficiency of such devices depend on the capillary wicking speed of solution across the antibody or reactant coated membrane, and the adequate wicking speed, superior handling, and reduced levels of non-specific binding of the membranes of the invention can accordingly provide a more accurate reading than devices currently available in the art.

Membrane Absorbent Device

Absorbent devices are disclosed generally in U.S. Pat. No. 4,125,372 to Kawai et al. the disclosure of which is incorporated by reference. The membranes of the invention, have superior porosity or void volume to many of the conventionally preferred absorptive materials described in the art, due to their highly asymmetric structure. Therefore, the membranes of the invention are well suited for substitution into such devices. Using the membrane-modified device of the invention and suitable reagents known to those skilled in the art, the presence of a variety of substances can be carried out with greater sensitivity than is currently possible in the art.

Other Devices

Similarly, occult blood testing devices and a variety of other biosensors can also be suitably modified to include the membranes of the invention as will be appreciated by those of skill in the art. It is expected that such modified devices will perform as well as, if not better than, current state of the art devices, sensors, and the like.

Filtration Systems

The polymeric membranes of the invention can also be advantageously substituted for microporous filters used in continuous laminar flow systems for separation of plasma from whole blood. A system of this type is disclosed in U.S. Pat. No. 4,212,742 to Solomon et al. which is hereby incorporated by reference. The membranes of the invention, have the ability to retain red blood cells in their larger pores and, therefore, appear to increase the separation efficiency of such laminar flow systems.

Similarly, the membranes of the invention can be used in a variety of other applications. A highly preferred embodiment of the invention, for example, is a membrane used for filtering the yeasts from beers and wines. Because of the unique structural aspects of the membranes, yeast cells tend to be collected in the pores, but the yeast is retained in substantially an intact form without falling apart. This reduces the bitterness of the flavor of the beers and wines.

In such applications, the membranes of the invention may be packaged and used in conventional applications. In this regard, the membranes of the invention have utility in applications currently served by classic asymmetric membranes such as the VARA-FINE™ filter cartridges, VARA-FINE™ filter capsules, and FILTERITE™ products that are manufactured and sold by MEMTEC AMERICA CORPORATION. In such products, the cartridges and/or capsules are prepared from potting the chosen membrane into a supporting housing. Usually, as will be appreciated, the membrane is pleated to increase the available surface area of the membrane. The housing is typically made from an inert material, such as simple polymer materials (i.e., polypropylene), specialty polymer materials (i.e., PVDF), or metals (i.e., stainless steel), depending on the end use of the filter assembly, for example, number of intended uses, environmental exposures, such as solvents, temperatures, filtrates, and the like, and pressures. Potting is usually accomplished through heat sealing or appropriate adhesives.

Typical applications of the above-described filtration systems are in the chemical, photographic, food, beverage, cosmetics, magnetic tape, and electronics industries. In such industries, the filtration systems are utilized in a variety of processes and contexts. For example, solvent filtration, acid filtration, deionized water preparation and filtration, beer and wine clarification, and a host of other uses. In general, since the membranes of the invention are so inert they can be used in almost any application. The membranes stand up well in extremely acid and extremely basic conditions, tolerate sanitizing and oxidizing agents well, and are thermally and chemically stable. As evidence of the extreme versatility and stability of the membranes, it is interesting to note that the membranes have been used with great success in filtration of hydrofluoric acid and sulfuric acid etching solutions from electronics industry waste streams. On the other end of the extreme, the membranes of the invention are capable of highly refined filtration in extreme organic exposure, such as in magnetic tape waste and supply streams.

EXAMPLES

The purpose, objects, and advantages of the membranes of the present invention will become more apparent through reference to the following Examples, Tables, and Figures. While the following Examples detail certain preferred features of the invention, they are intended to be exemplary and not limiting of the invention in any way.

EXAMPLE 1

PREPARATION OF LARGE PORE ASYMMETRIC POLYSULFONE MEMBRANE USING STANDARD WRASIDLO BTS-45 (0.2 $\mu$M) FORMULATION

A membrane of the invention having large diameter skin surface pores was prepared as described below. In general, the membrane was prepared from a standard Wrasidlo polysulfone formulation that is used to prepare highly asymmetric membranes having a bubble point of 45 psid. The casting technique to prepare the membranes of the invention was similar. However, the air gap was increased and the relative humidity of the cast was monitored. The formulation was as follows:

| Formulation: | |
|---|---|
| Dimethyl formamide (DMF, solvent) | 73.72% |
| tertiary-amyl alcohol | 15.56% |
| Polysulfone (AMOCO P3500) | 10.75% |
| Casting Index | .173 |

The formulation was cast in an automatic casting machine (conventional diagnostic grade). The formulation was spread using a spreading knife onto polyethylene coated paper under the following conditions:

| Casting Conditions: | |
|---|---|
| Casting dope temperature | 105° F. (41° C.) |
| Quench water temperature | 118° F. (47.7° C.) |
| Air gap | 6 in |
| Casting speed | 20 ft/min |
| Room temperature | 77° F. (25° C.) |
| Relative humidity | 59% |

Following drying of the resultant membrane, the membrane was recovered. The recovered membrane had the following properties:

| Properties: | |
|---|---|
| Bubble point | 8-psid |
| Water flow rate | 19.9 cm/min-psid |
| Mean flow pore size | 0.9 $\mu$m |
| Thickness | 121 $\mu$m |
| Breaking strength | 454 g/cm |
| Elongation | 27% |

The casting dope, as indicated by the index, was stable. The resultant membrane had a uniform, defect-free surface appearance. Thickness, breaking strength, and elongation were typical of the standard BTS-45 product. However, in contrast to the typical BTS-45 product, the membrane had a significantly lower bubble point with highly improved flow rates. This membrane is referred to herein as Sample A.

EXAMPLE 2

PREPARATION OF MEMBRANES OF THE INVENTION HAVING DIVERSE BUBBLE POINTS

Two additional membranes were prepared in accordance with Example 1. The air gap was decreased slightly, down to 5.5 inches and 5 inches, respectively, and two membranes having different bubble points were obtained. The membrane prepared with a 5.5 inch air gap had a bubble point of 11 psid (Sample B), while the membrane prepared with the 5 inch air gap had a bubble point of 16 psid (Sample C).

Other than the difference in bubble point, the Sample B and Sample C membranes had similar properties to the Sample A membrane prepared in Example 1.

EXAMPLE 3

SCANNING ELECTRON MICROSCOPY OF THE MEMBRANES PREPARED IN EXAMPLES 1 AND 2

Scanning electron micrographs were prepared from the membranes synthesized in Example 1 and 2. Generally, micrographs of the skin surface, the casting surface, and the cross section of the membranes were taken. The samples were cut and sputtered with gold using conventional techniques. The micrographs were prepared on a JEOL Model No. 5200 Scanning Electron Microscope equipped with a Polaroid Camera. The results of the micrographs are shown in FIGS. 1 through 3.

FIG. 1a shows a skin surface micrograph taken at 5,000× of the membrane of Sample A, which had a bubble point of 8 psid. FIG. 1b is a cast surface micrograph taken at 1,500×, and FIG. 1c is a cross-sectional micrograph taken at 500×of the same membrane.

Figure 2A:
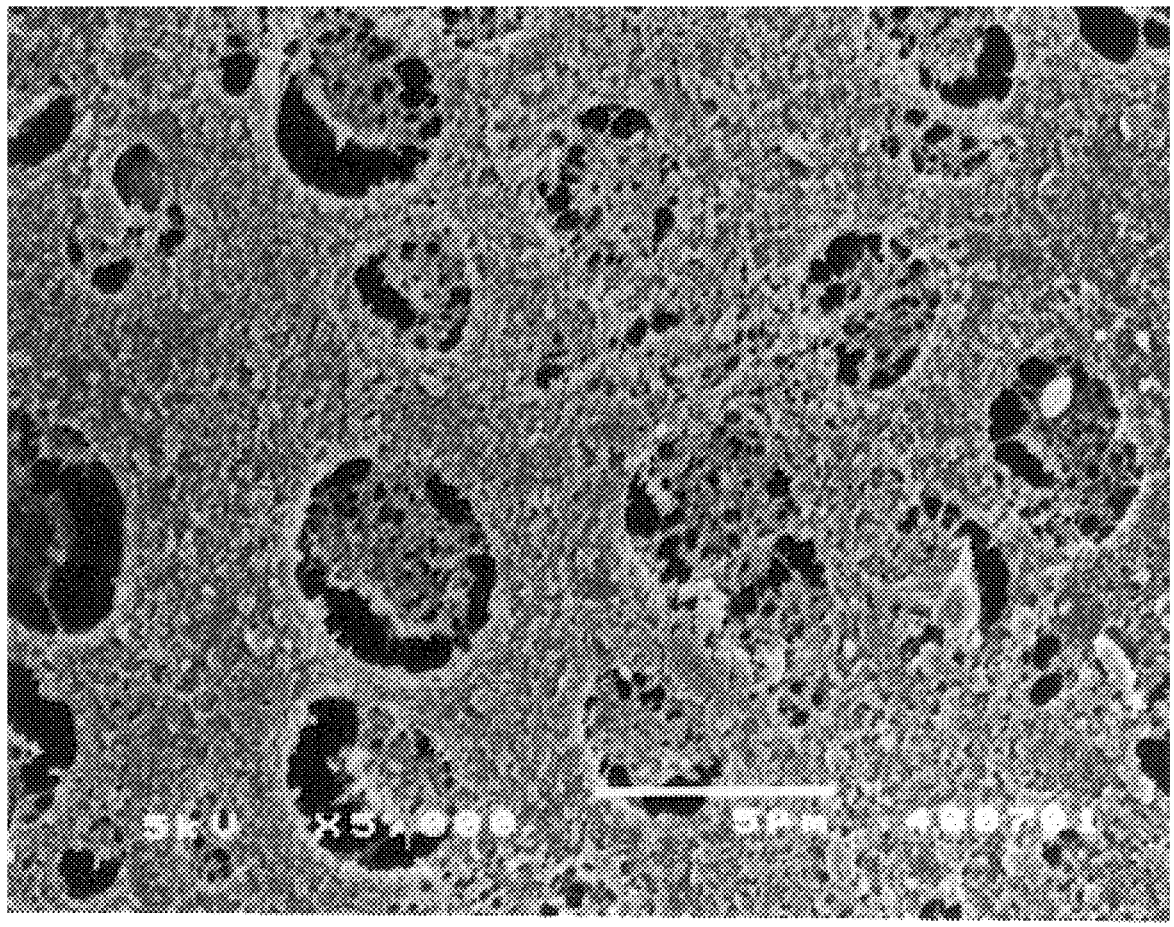
FIGS. 2a, 2b, 2c are a series of scanning electron microscope images of an open pored membrane prepared in accordance with the invention from a polysulfone polymer dispersion (Wrasidlo-type) that has a bubble point of 11 psid.
Figure 2B:
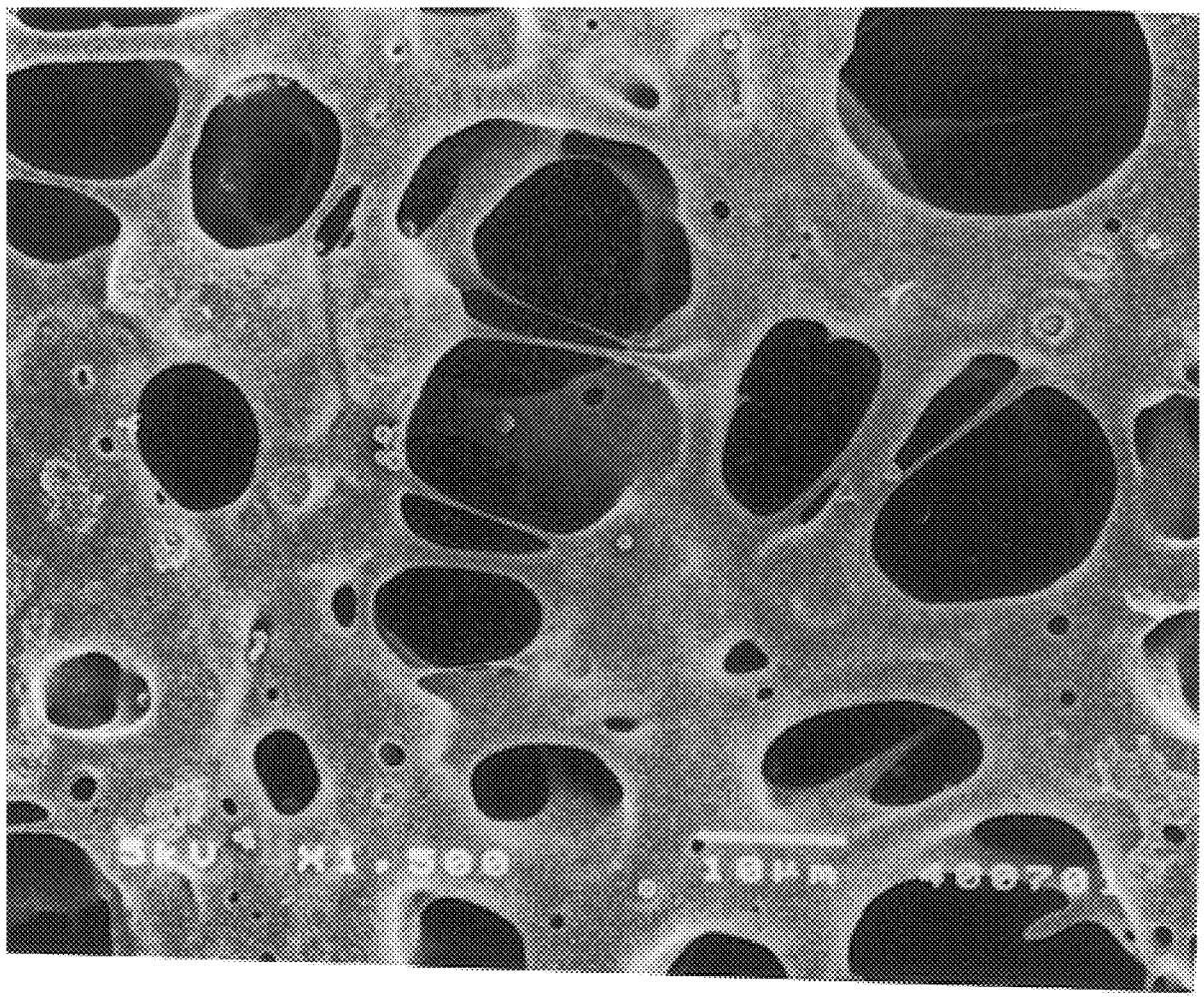
Figure 2C:
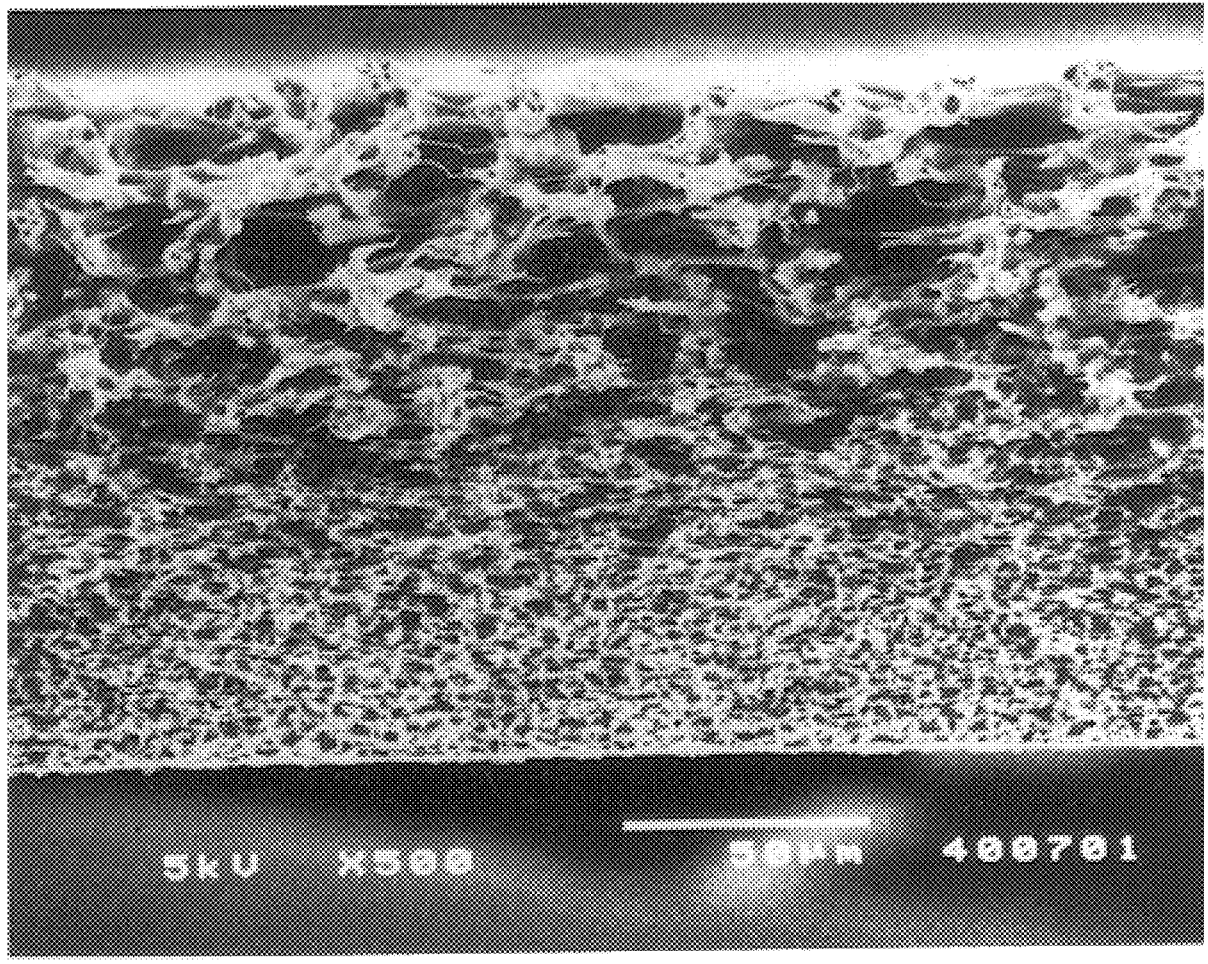

FIG. 2a shows a skin surface micrograph taken at 5,000× of the membrane of Sample B, which had a bubble point of 8 psid. FIG. 2b is a cast surface micrograph taken at 1,500×, and FIG. 2c is a cross-sectional micrograph taken at 500×of the same membrane.

Figure 3A:
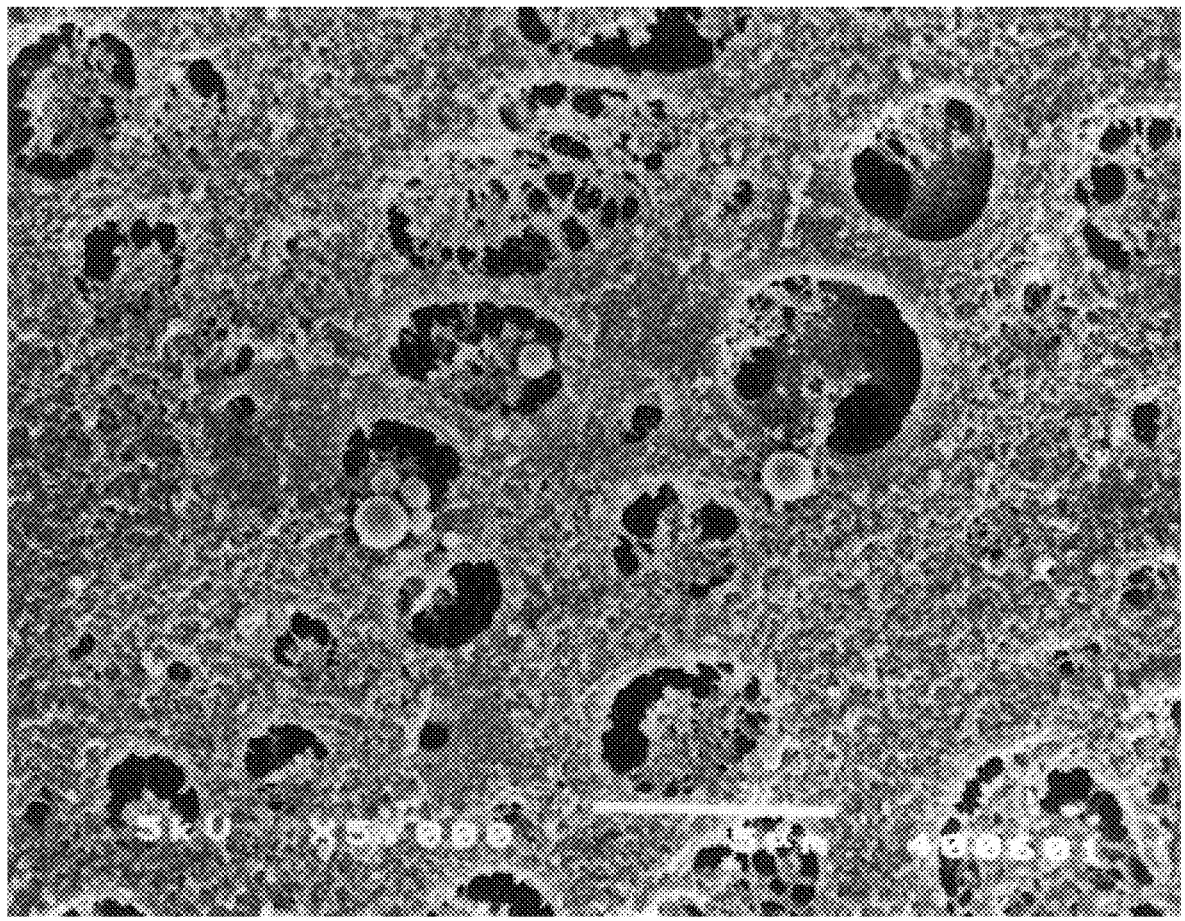
FIGS. 3a, 3b, 3c are a series of scanning electron microscope images of an open pored membrane prepared in accordance with the invention from a polysulfone polymer dispersion (Wrasidlo-type) that has a bubble point of 16 psid.
Figure 3B:
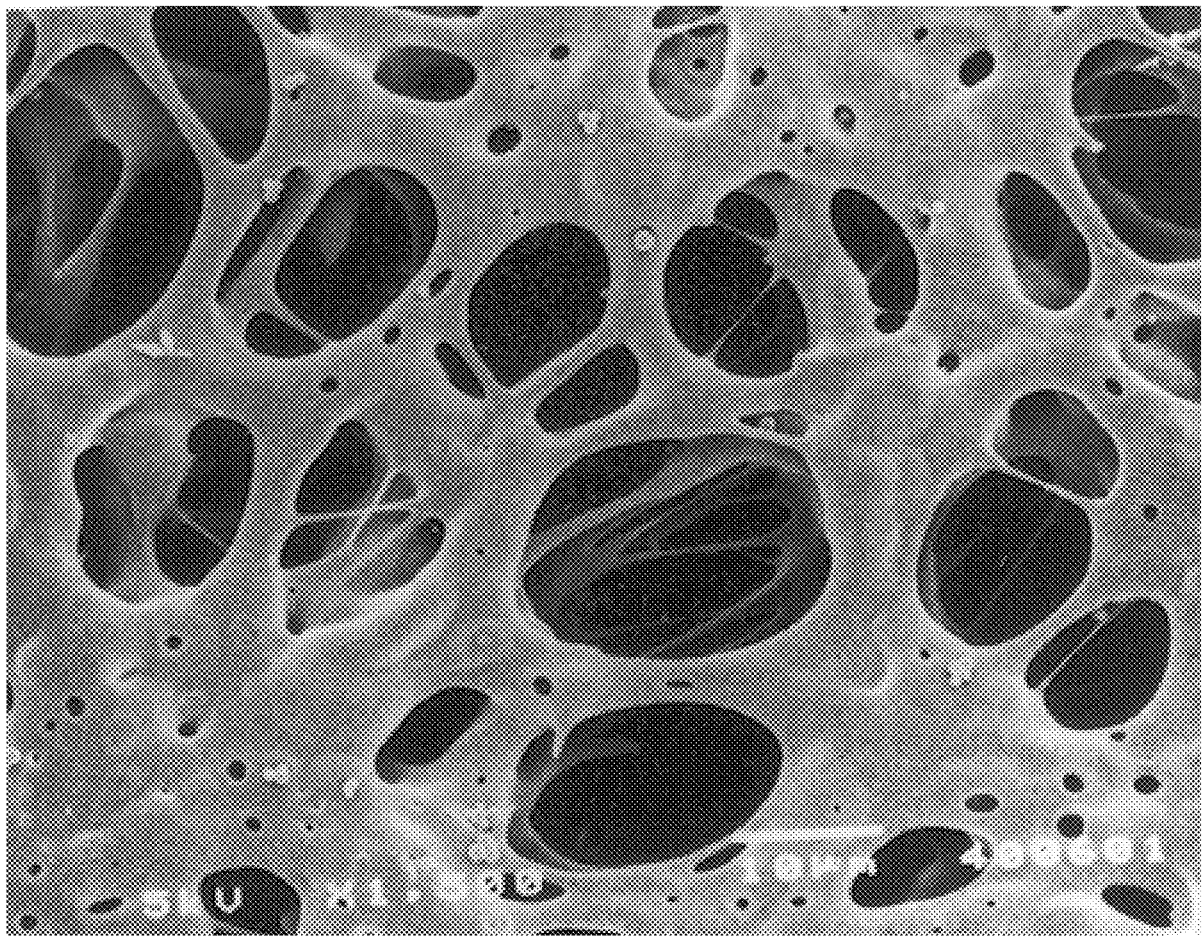
Figure 3C:
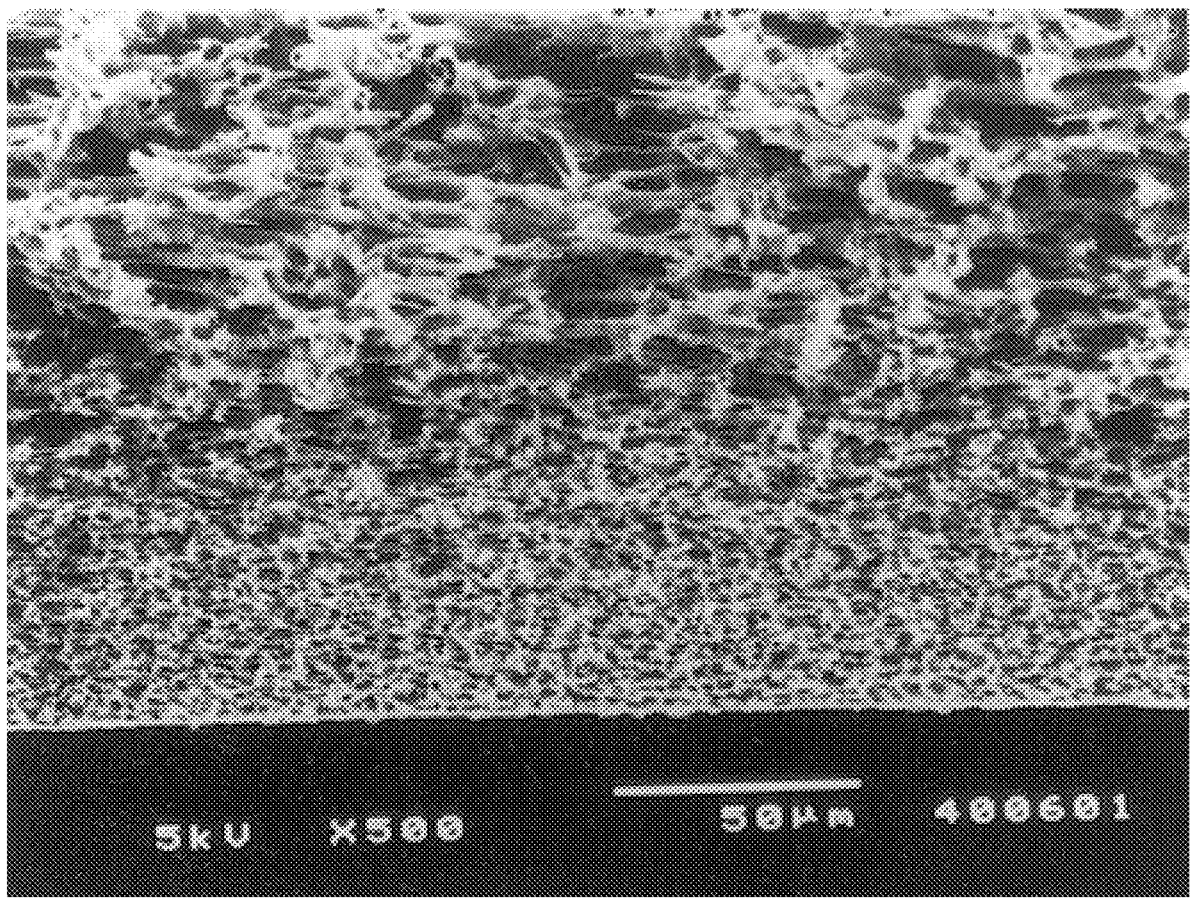

FIG. 3a shows a skin surface micrograph taken at 5,000× of the membrane of Sample C, which had a bubble point of 8 psid. FIG. 3b is a cast surface micrograph taken at 1,500×, and FIG. 3c is a cross-sectional micrograph taken at 500×of the same membrane.

As will be seen, in each of the cross-sectional views, the membranes exhibit a generally isotropic region in the area below and including the skin surface. This isotropic region appears to extend through greater than a quarter of the membrane thickness and perhaps as much as a third of the membrane thickness. Below the isotropic region, the membranes have an asymmetric region.

The degree of asymmetry of the membranes is most clearly seen through looking at the surface micrographs, where the pore sizes at the surfaces can be observed. In Sample A, FIGS. 1a and 1b, on average, the pore sizes are approximately 3 μm on the skin surface and 20 μm on the cast surface. Sample B, in FIGS. 2a and 2b, on average, the pore sizes are approximately 2.5 μm on the skin surface and 15 μm on the cast surface. And, in Sample C, FIGS. 3a and 3b, on average, the pore sizes are approximately 2 μm on the skin surface and 12 μm on the cast surface. In each case, the degree of asymmetry is approximately 1:6. Recall, however, that this degree of asymmetry occurs in the last two-thirds to three-quarters of the thickness of the membrane, so the pore ratio is not as great as if it had progressively spread through the total thickness of the membrane.

EXAMPLE 4

PREPARATION OF ZEPF-TYPE MEMBRANES HAVING DIVERSE BUBBLE POINTS

In addition to the above formulations, two conventional Zepf-type membranes were prepared. The membranes were prepared in accordance with the Zepf patent, Example 2, with an air gap of less than one inch. The resultant membranes had bubble points of 25 and 65 psid, respectively, and are referred to herein as Sample D and Sample E.

Figure 5A:
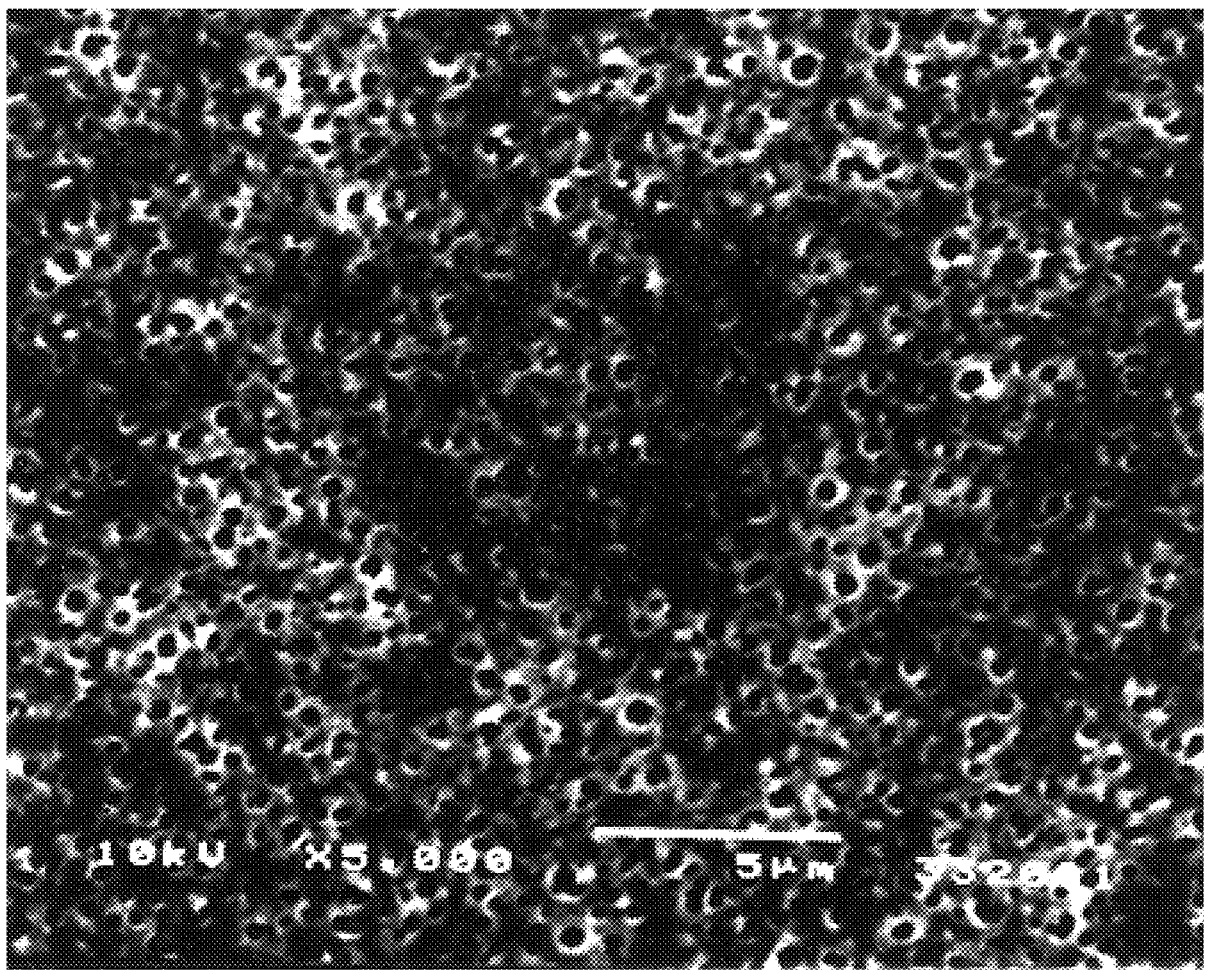
FIGS. 5a, 5b, 5c are a series of scanning electron microscope images of a fine pored polysulfone membrane prepared in accordance with the method of Zepf and having a bubble point value of 65.
Figure 5B:
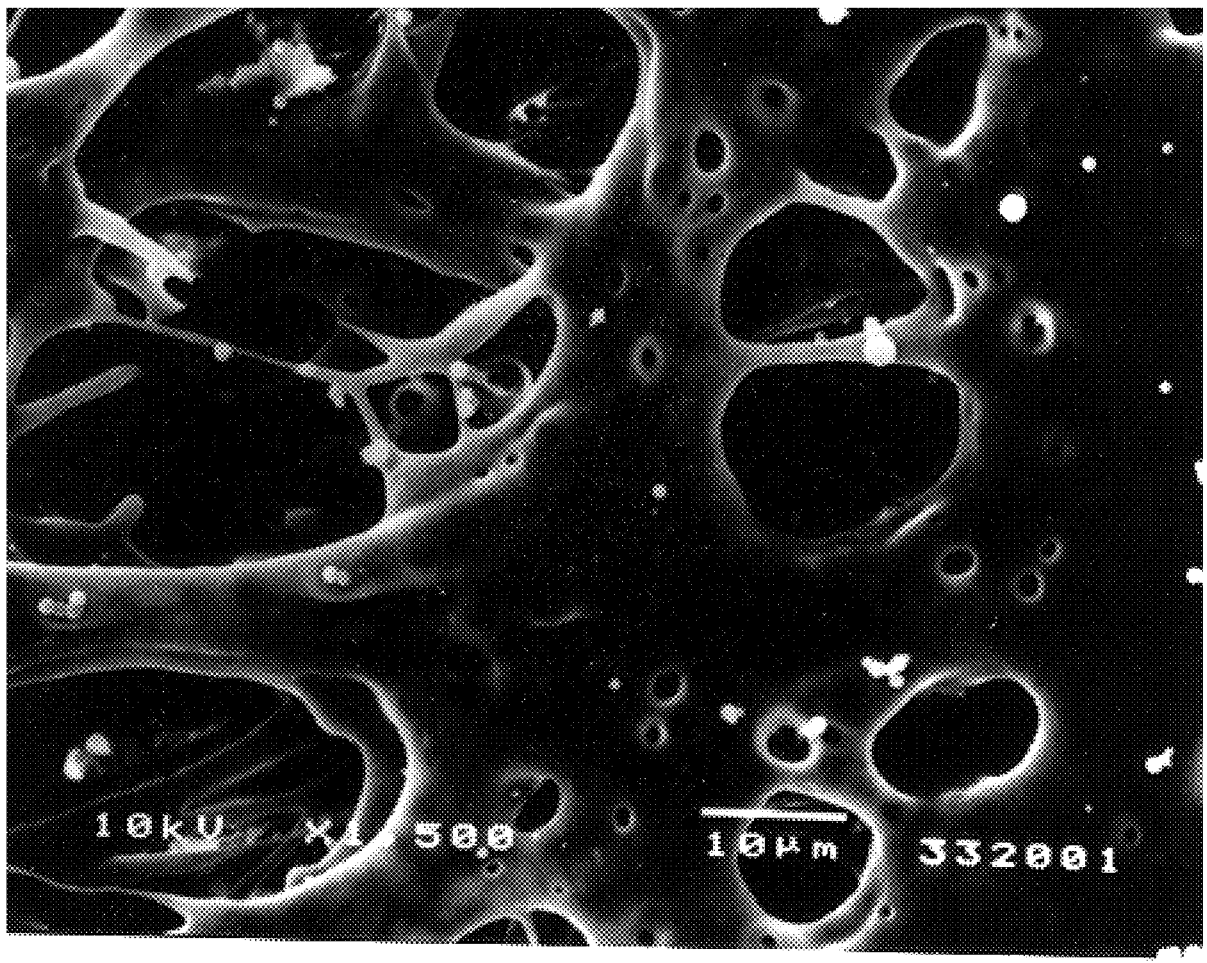
Figure 5C:
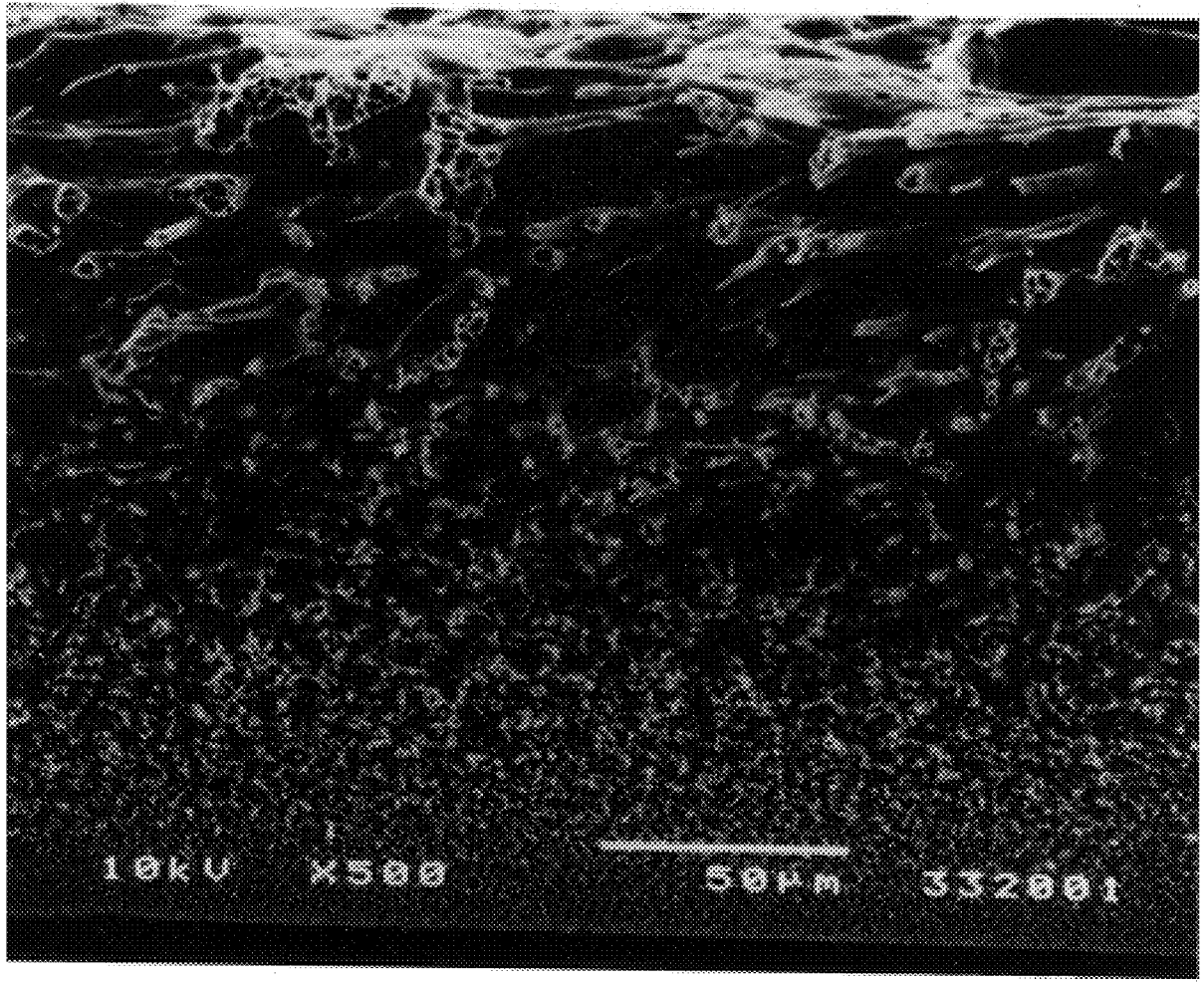
Figure 6:
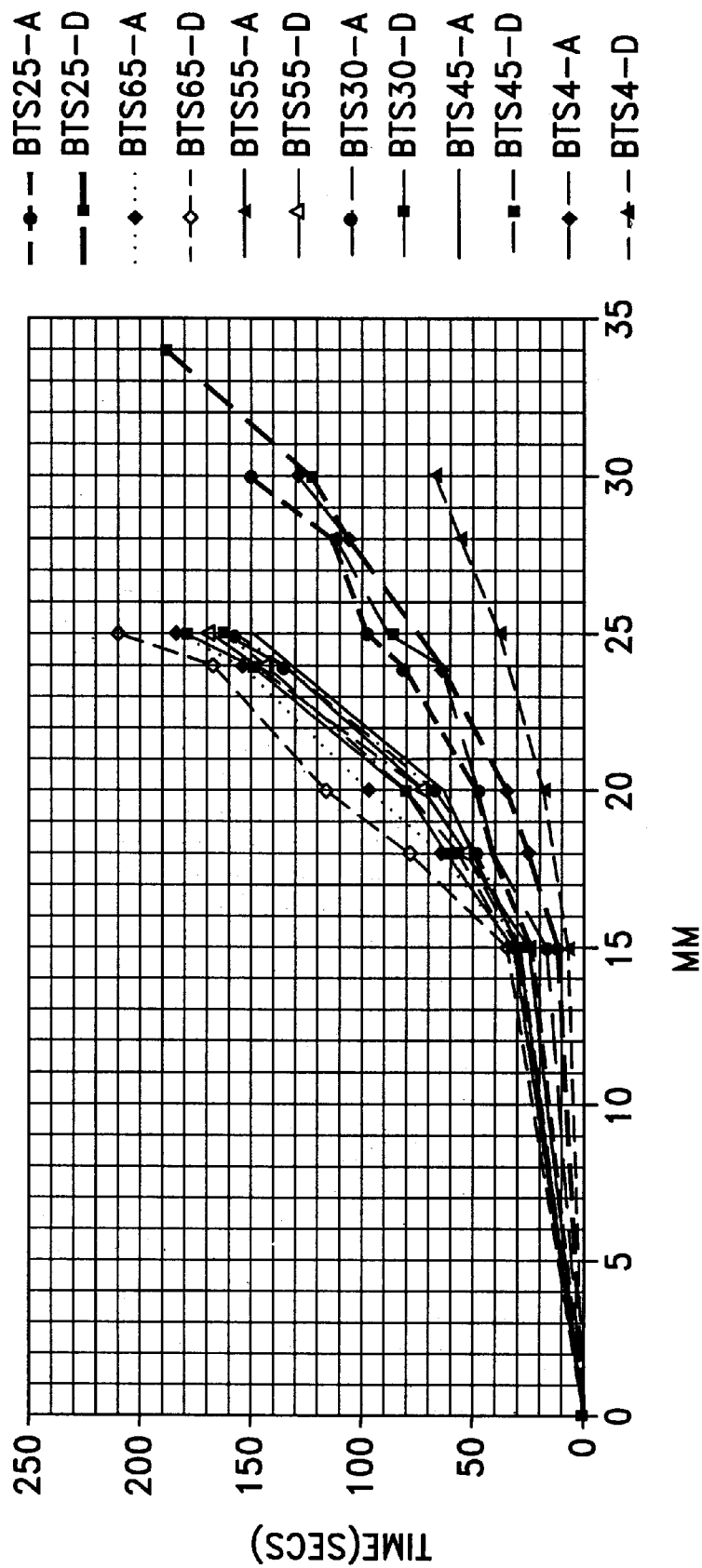
FIG. 6 is a graph showing the rate at which a liquid front travels while migrating laterally in a series of membranes having various BTS (bubble point) values.
Figure 7:
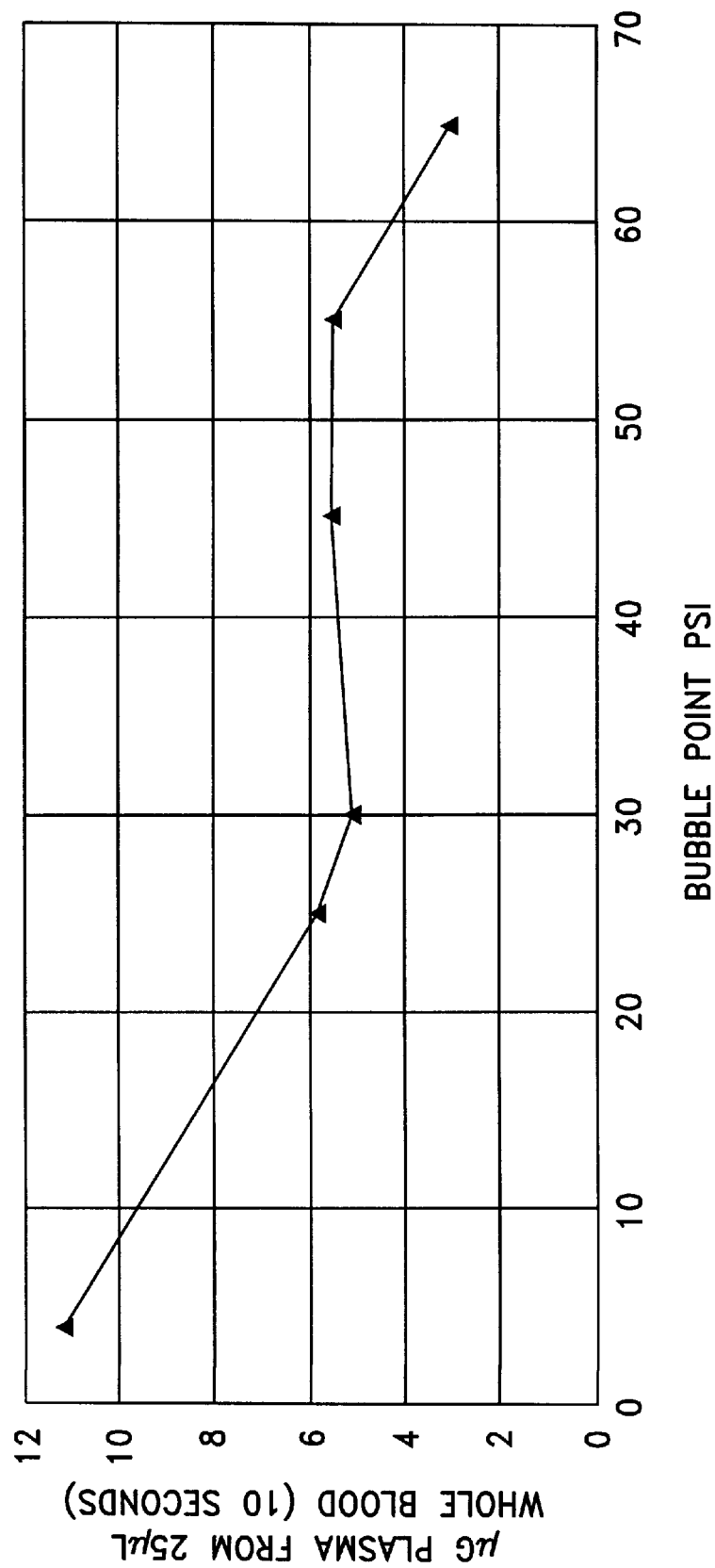
FIG. 7 is a graph showing the volume of red cell-free plasma filtrate that is delivered from polysulfone membranes of various bubble points in 10 seconds.

SEM's of the membranes showed classical Zepf membrane structure. FIGS. 5a through 5c are SEM's showing the skin surface, the cast surface, and the cross-section of the Sample E membrane, which has a bubble point of 65 psid. In FIG. 5a, which is the skin surface micrograph of the Sample E membrane, the pores are clearly smaller than 1 μm, and, on average, are 0.3 μm in mean diameter. In the cross-sectional view, FIG. 5c, the complete asymmetry of the membrane is seen. The pore sizes gradually increase from the skin surface to the cast surface. The porosity of the cast surface is shown in FIG. 5b. The size of the pores on the cast surface, on average, are 20 μm in mean diameter.

EXAMPLE 5

PORE SIZES BASED ON SEM ANALYSES

The pore sizes of the various membranes prepared above, were analyzed in an effort to provide a quantitative determination of their sizes. The results of the analysis is presented in the following Table:

TABLE I

| Sample | FIGS. | Skin Surface | Cast Surface |
|---|---|---|---|
| A | 1a and 1b | 3 μm | 20 μm |
| B | 2a and 2b | 2.5 μm | 15 μm |
| C | 3a and 3b | 2 μm | 12 μm |
| E | 5a and 5b | 0.3 μm | 20 μm |

EXAMPLE 6

COULTER DATA

The structures of several of the membranes in the Examples were characterized using a Coulter porometer, Model No. 0204. The results are shown in the following Table.

TABLE II

| Characteristic | Sample A* | Sample B* | Sample C* | Sample D* | Sample E* |
|---|---|---|---|---|---|
| Bubble Point (psid) | 8 | 11 | 16 | 25 | 65 |
| Thickness (μm) | 124.67 | 127.7 | 118 | 138.3 | 134.3 |
| Weight (mg) | 16.7 | 17.2 | 16.03 | 16.07 | 19.4 |
| Dead Volume (cc) | 0.0505 | 0.0516 | 0.0476 | 0.0579 | 0.0533 |
| Percent Porosity | 79.2494 | 79.1271 | 78.9515 | 82.0057 | 77.6295 |
| Minimum Pore Size | 0.8433 | 0.7687 | 0.8030 | 0.3763 | 0.1390 |
| Maximum Pore Size | 1.2027 | 1.0423 | 1.1885 | 0.5303 | 0.2460 |
| Mean Pore Size | 0.9970 | 0.8447 | 0.9450 | 0.4443 | 0.2040 |
| Diffusive Number of Pores at MPFS | $3.55 \times 10^7$ | $6.08 \times 10^7$ | $3.47 \times 10^7$ | $5.14 \times 10^8$ | $6.66 \times 10^9$ |
| Maximum Diffusive Number of Pores | $4.05 \times 10^7$ | $8.11 \times 10^7$ | $3.69 \times 10^7$ | $5.18 \times 10^8$ | $6.74 \times 10^9$ |
| Total Number of Pores | $1.58 \times 10^9$ | $1.87 \times 10^9$ | $1.45 \times 10^9$ | $2.72 \times 10^{10}$ | $4.25 \times 10^{11}$ |
| Diffusive Flow at MPFS | 2.3013 | 3.2293 | 2.3883 | 1.9323 | 2.1237 |
| Maximum Diffusive Flow | 2.3550 | 3.5923 | 2.3997 | 1.9630 | 2.1827 |

EXAMPLE 7

COMPARISON OF COULTER DATA TO EMPIRICAL DATA

A striking structural feature or phenomenon of the membranes of the invention is that the Coulter data differs markedly from the actual physical structure of the membranes as determined empirically from SEM's of the membranes. For example, in the following Table, the minimum, maximum, and mean pore sizes as determined by Coulter are contrasted to measurements from the SEM's of the membranes.

TABLE III

| | BUBBLE POINT | COULTER DATA | | | EMPIRICAL Skin Pore Size v. Open Pore Size |
|---|---|---|---|---|---|
| | | Minimum | Maximum | Mean | |
| Sample A | 8 psid | 0.8433 | 1.2027 | 0.9970 | 3/20 |
| Sample B | 11 psid | 0.7677 | 1.0423 | 0.8447 | 2.5/15 |
| Sample C | 16 psid | 0.8030 | 1.1885 | 0.9450 | 2/12 |

As will be observed, in Coulter analysis, the membranes appear to have similar pore sizes. Yet, empirically the membranes have very different surface structures from one another. Further, the maximum and minimum pore sizes seen in Coulter analysis is not even approximated in the SEM cross-sectional views of the membranes. Also, the bubble point in view of the open pore structure would be expected to be lower than the observed or actual bubble point.

EXAMPLE 8

PREPARATION OF POLYSULFONE MEMBRANES FROM HOMOGENEOUS SOLUTIONS

Laboratory casting of a homogeneous solution of 9% polysulfone (Amoco P-3500), 19% 2-methoxyethanol, and 72% dimethylformamide yielded a membrane with a bubble point of 72 psid when cast with 0.25 second exposure to humid air (temperature 22° C., relative humidity 44%) before quenching in water (45° C.). The same formulation gave a membrane with a 12-psid bubble point when subjected to 4 seconds exposure to air at 22° C. and 60% relative humidity. The casting operation was carried out using conventional diagnostic grade casting equipment with a plastic tent around the unit to increase the humidity.

EXAMPLE 9

SCANNING ELECTRON MICROSCOPY OF THE MEMBRANE OF THE INVENTION PREPARED IN EXAMPLE 7

Scanning electron micrographs were prepared from the membrane of the invention that was prepared in Example 7. As mentioned, this membrane had a bubble point of 12 psid. The SEM's were run in accordance with Example 3. The results of the SEM's are shown in FIG. 4. As will be appreciated, the membrane has an open skin surface pore structure (FIG. 4a). Also, the cast surface pore structure is very open, demonstrating substantial asymmetry (FIG. 4b). On cross-section, the membrane is similar to the dispersed formulation membranes in the presence of the isotropic region and the asymmetric region (FIG. 4c).

EXAMPLE 10

PREPARATION OF OTHER MEMBRANES OF THE INVENTION FROM HOMOGENEOUS FORMULATIONS

Several different homogeneous polymer solutions were prepared and cast into sheet membranes according to the procedure set forth in Example 2. Exposure to humid air was varied as described in Annex I.

EXAMPLE 11

BIOLOGICAL USES OF THE MEMBRANES OF THE INVENTION

I. Lateral Wicking on Open-pore Membrane Prepared from a Phase Inversion Formulation:

A quantity of 60 µl of sheep whole blood was applied to the open dull side of 1×4 cm strips of asymmetric membrane of BTS range of from BTS-25 to BTS-65 as well as the open pore BTS-4 membrane prepared as described in Example 9, and a reading was taken of the time required for the plasma front to reach a set distance from the point of application for each membrane. Both across web (A) and down web (D) samples were investigated. The results are shown in FIG. 4.

A. Lateral wicking: A quantity of 60 µl of sheep whole blood was applied to a 1×4 cm strip of a BTS 8 membrane prepared by the method of Example 1. The plasma front had travelled a distance of 25 mm in 40 sec. By comparison, the rate of lateral wicking on tight pore membranes was 25 mm in 180 sec.

B. Vertical Separation: A quantity of 25 µl of sheep whole blood was applied to the dull side of the membrane as described in (a) having a surface area of 1 $cm^2$. The weight of plasma drawn off the tight side and absorbed into filter paper was approximately 10 mg.

C. Protein Binding: Protein determinations were made for the following enzymes according to the Pierce BCA protein test and the optical density read at $\lambda$=562 nm. Sensitivity of the assay was 1 ug/ml, and protein on the membranes could be read at <0.3 mg/$cm^2$.

1. Acid phosphatase at concentrations of 100–500 µg/ml showed less than or equal to 10% adsorption to the membrane when filtered through a 47 mm disk of the filter materials prepared as indicated in Examples 1–4 at 0–10 psi and across a pH range of 4.5–9.5.
2. Malate dehydrogenase at concentrations of 100–500 µg/ml showed less than or equal to 10% adsorption to the membrane when filtered through a 47 mm disk of the filter materials prepared as indicated in Examples 1–4 at 0–10 psi and across a pH range of 4.5–9.5.
3. Lactate Dehydrogenase at concentrations of 100–500 µg/ml showed less than or equal to 10% adsorption to the membrane when filtered through a 47 mm disk of the filter materials prepared as indicated in Examples 1–4 at 0–10 psi and across a pH range of 4.5–9.5.

EQUIVALENTS

While the invention has been described in terms of certain preferred embodiments and with reference to certain specific Examples and Figures, the invention is not limited thereby. Accordingly, no matter how detailed the foregoing may appear in text, the scope of the invention should be construed only with reference to the appended claims and any equivalents thereof.

ANNEX I

| No. | Formulation Number | % Solvent Conc. | % Polymer Conc. | Non-Solvent Composition | Non-Solvent Conc. % | °C. Water Quench | °C. Air Temp. | % Rel. Humid. | Casting Speed (ft/min) | Air Gap IN | Exposure Time In Air-Sec | Bubble Points (PSI) | Water Flow CM/MIN-PSI | Comments |
|---|---|---|---|---|---|---|---|---|---|---|---|---|---|---|
| 1. | 0429-3-1A | 72 | 9 | MeOEtOH | 19 | 45 | — | LOW | 17 | 1 | 0.3 | 57 | 3.8 | HUMIDITY TENT |
| 2. | 0429-3-1B | 72 | 9 | MeOEtOH | 19 | 45 | — | HIGH | 10 | 10 | 5 | 13,16 | 8.5 | OVER CASTING TANK |
| 3. | 0622-3-1A | 72 | 9 | MeOEtOH | 19 | 45 | 24 | 56 | 20 | 17 | 4.25 | 4 | 19.2 | WITH HUMIDITY TENT |
| 4. | 0622-3-1B | 72 | 9 | MeOEtOH | 19 | 45 | 24 | 52 | 10 | 17 | 8.5 | 6 | 13.1 | WITH HUMIDITY TENT |
| 5. | 0622-3-2A | 72 | 9 | MeOEtOH/PVP | 9.5/9.5 | 45 | 24 | 56 | 20 | 17 | 4.25 | 14 | 9.4 | WITH HUMIDITY TENT |
| 6. | 0622-3-2B | 72 | 9 | MeOEtOH/PVP | 9.5/9.5 | 45 | 24 | 52 | 10 | 17 | 8.5 | 19 | 7.1 | WITH HUMIDITY TENT |
| 7. | 0622-3-3A | 72 | 9 | MeOEtOH/PEG | 9.5/9.5 | 45 | 24 | 56 | 20 | 17 | 4.25 | 34 | 6.0 | WITH HUMIDITY TENT |
| 8. | 0622-3-3B | 72 | 9 | MeOEtOH/PEG | 9.5/9.5 | 45 | 24 | 52 | 10 | 17 | 8.5 | 70 | 4.5 | WITH HUMIDITY TENT |
| 9. | 0623-3-6A | 71.8 | 8.8 | MeOEtOH | 19.3 | 45 | 24 | 50 | 10 | 7 | 3.5 | 30 | 4.8 | WITH HUMIDITY TENT |
| 10. | 0623-3-6B | 71.8 | 8.9 | MeOEtOH | 19.3 | 45 | 24 | 55 | 10 | 7 | 3.5 | 18 | 6.6 | WITH HUMIDITY TENT |
| 11. | 0623-3-6C | 71.8 | 8.9 | MeOEtOH | 19.3 | 45 | 24 | 61 | 10 | 7 | 3.5 | 11,15 | 7.0 | WITH HUMIDITY TENT |
| 12. | 0628-3-2A | 71.1 | 8.9 | MeOEtOH/PEG | 18/2 | 45 | 24 | 55 | 10 | 8 | 4 | 4–9 | 12.3 | WITH HUMIDITY TENT |
| 13. | 0628-3-2B | 71.1 | 8.9 | MeOEtOH/PEG | 18/2 | 45 | 24 | 55 | 17 | 8 | 2.4 | 13–17 | 9.4 | WITH HUMIDITY TENT |
| 14. | 0706-3-1B | 72 | 9 | MeOEtOH | 19 | 46 | 22 | 62 | 20 | 9 | 2.25 | 4,8,4,3 | 8.3 | FAN BLOWING (175 FPM) |
| 15. | 0706-3-1C | 72 | 9 | MeOEtOH | 19 | 46 | 22 | 62 | 10 | 9 | 4.5 | 1,2,3 | 19.0 | FAN BLOWING (175 FPM) |
| 16. | 0706-3-1D | 72 | 9 | MeOEtOH | 19 | 46 | 22 | 62 | 10 | 1 | 0.5 | 44 | 4.5 | FAN BLOWING (175 FPM) |
| 17. | D714-3-4D | 72 | 9 | MeOEtOH/PEG | 14/5 | 45 | 22 | 60 | 10 | 8 | 4 | 4 | 20.6 | HUMIDITY TENT |
| 18. | D714-3-5D | 72 | 9 | MeOEtOH/PVP | 14/5 | 45 | 22 | 60 | 8 | 8 | 21 | 8.1 | HUMIDITY TENT |
| 19. | 0824-3-2A | 68.5 | 9 | BuOEtOH | 22.5 | 45 | — | 72 | 10 | 10 | 5 | 2.5,8.5,12 | 10.9 | FAN ACROSS WATER; WITH TENT |
| 20. | 0824-3-2B | 68.5 | 9 | BuOEtOH | 22.5 | 45 | — | 72 | 20 | 1 | 0.25 | 15,35 | 3.3,2.9 | FAN ACROSS WATER; WITH TENT |

*B.P.'s > EXTRAPOLATED FROM 50/50 IPA/H$_2$O BUBBLE POINT (2X)
***CASTING SOLUTIONS PRE-HEATED TO 40° C.

What we claim is:

1. In a diagnostic device comprising a filtering means that delivers a filtrate that is substantially particle free containing an analyte to an analyte-detecting region of the device, the improvement comprising:

a filtering means comprising a polymer membrane, the membrane comprising a minimum porous surface, an opposite porous surface, and a porous supporting structure therebetween, wherein the minimum surface comprises a relatively open pore structure and the opposite surface comprises a more open pore structure and wherein the supporting structure comprises a high degree of asymmetry through at least 50% of the supporting structure but no more than 80% of the supporting structure, the membrane having surface pores at the minimum surface of a mean diameter of at least about 1.2 microns and having a flow rate of greater than about 4.5 cm/min/psi; and a sample application area that directs sample first to the opposite surface.

2. The device according to claim 1, wherein the membrane has a bubble point of from about 0.5 psid to about 25 psid.

3. The device according to claim 1, wherein the membrane has a mean aqueous flow rate of from about 4.5 to 25 cm/min psid.

4. In a diagnostic device comprising a lateral wicking means that transfers a sample that is substantially particle free containing an analyte from a sample receiving region of the device to an analyte-detecting region of the device, the improvement comprising:

a lateral wicking means comprising a polymer membrane, the membrane comprising a minimum porous surface, an opposite porous surface, and a porous supporting structure therebetween, wherein the minimum surface comprises a relatively open pore structure and the opposite surface comprises a more open pore structure and wherein the supporting structure comprises a high degree of asymmetry through at least 50% of the supporting structure but no more than 80% of the supporting structure, the membrane having surface pores at the minimum surface of a mean diameter of at least about 1.2 microns and having a lateral transfer rate of greater than about 2 cm per minute; and a sample application area that directs sample first to the opposite surface.

5. The device according to claim 4, wherein the membrane has a bubble point of from about 0.5 psid to about 25 psid.

6. The device according to claim 4, wherein the membrane has a mean aqueosus flow rate of from about 4.5 to 25 cm/min psid.

7. In a diagnostic device comprising a filtering means that delivers a filtrate that is substantially particle free containing an analyte to an analyte-detecting region of the device, the improvement comprising:

a filtering means comprising a polymer membrane, the membrane comprising a minimum porous surface, an opposite porous surface, and a porous supporting structure having a thickness therebetween, wherein the supporting structure has a generally isotropic structure from the minimum surface to a point at about one-quarter of the thickness of the supporting structure and a generally asymmetric structure from the point to the opposite surface, the membrane having surface pores at the minimum surface of a mean diameter of at least about 1.2 microns and having a flow rate of greater than about 4.5 cm/min/psi; and a sample application area that directs sample first to the opposite surface.

8. The device according to claim 7, wherein the membrane has a bubble point of from about 0.5 psid to about 25 psid.

9. The device according to claim 7, wherein the membrane has a mean aqueous flow rate of from about 4.5 to 25 cm/min psid.

10. In a diagnostic device comprising a filtering means that delivers a filtrate that is substantially particle free containing an analyte to an analyte-detecting region of the device, the improvement comprising:

a filtering means comprising a polymer membrane, the membrane comprising a minimum porous surface, an opposite porous surface, and a supporting structure having a thickness therebetween, the supporting structure defining porous flow channels between the minimum surface and the opposite surface, wherein the flow channels have a substantially constant mean diameter from the minimum surface to a point at about one-quarter of the thickness of the supporting structure and an increasing mean diameter from the point to the opposite surface, the membrane having surface pores at the minimum surface of a mean diameter of at least about 1.2 microns and having a flow rate of greater than about 4.5 cm/min/psi; and a sample application area that directs sample first to the opposite surface.

11. The device according to claim 10, wherein the membrane has a bubble point of from about 0.5 psid to about 25 psid.

12. The device according to claim 10, wherein the membrane has a mean aqueous flow rate of from about 4.5 to 25 cm/min psid.

13. In a diagnostic device comprising a filtering means that delivers a filtrate that is substantially particle free containing an analyte to an analyte-detecting region of the device, the improvement comprising:

a filtering means comprising a polymer membrane, the membrane comprising an integral porous skin, lying at one face of the membrane, wherein substantially all of the pores of the skin have diameters greater than about 1.2 microns, and a support region of the membrane lying below the skin and having an asymmetric structure, the membrane having a flow rate of greater than about 4.5 cm/min/psi; and a sample application area that directs sample first to the opposite surface.

14. The device according to claim 13, wherein the membrane has a bubble point of from about 0.5 psid to about 25 psid.

15. The device according to claim 13, wherein the membrane has a mean aqueous flow rate of from about 4.5 to 25 cm/min psid.

16. In a diagnostic device comprising a filtering means that delivers a filtrate that is substantially particle free containing an analyte to an analyte-detecting region of the device, the improvement comprising:

a filtering means comprising an improved asymmetric polymer membrane having a minimum porous surface, an opposite porous surface, and a porous supporting structure therebetween and having a thickness, the membrane comprising:

a region of generally isotropic structure from the minimum surface to a point at about one-quarter of the thickness of the supporting structure, the membrane having surface pores at the minimum surface of a mean diameter of at least about 1.2 microns and having a flow rate of greater than about 4.5 cm/min/psid; and a sample application area that directs sample first to the opposite surface.

17. The device according to claim 16, wherein the membrane has a bubble point of from, about 0.5 psid to about 25 psid.

18. The device according to claim 16, wherein the membrane has a mean aqueous flow rate of from about 4.5 to 25 cm/min psid.

19. In a diagnostic device comprising a lateral wicking means that transfers a sample that is substantially particle free containing an analyte from a sample receiving region of the device to an analyte-detecting region of the device, the improvement comprising:

a lateral wicking means comprising a polymer membrane, the membrane comprising a minimum porous surface, an opposite porous surface, and a porous supporting structure having a thickness therebetween, wherein the supporting structure has a generally isotropic structure from the minimum surface to a point at about one-quarter of the thickness of the supporting structure and a generally asymmetric structure from the point to the opposite surface, the membrane having surface pores at the minimum surface of a mean diameter of at least about 1.2 microns and having a lateral transfer rate of greater than about 2 cm per minute; and a sample application area that directs sample first to the opposite surface.

20. The device according to claim 19, wherein the membrane has a bubble point of from about 0.5 psid to about 25 psid.

21. The device according to claim 19, wherein the membrane has a mean aqueous flow rate of from about 4.5 to 25 cm/min psid.

22. In a diagnostic device comprising a lateral wicking means that transfers a sample that is substantially particle free containing an analyte from a sample receiving region of the device to an analyte-detecting region of the device, the improvement comprising:

a lateral wicking means comprising a polymer membrane, the membrane comprising a minimum porous surface, an opposite porous surface, and a supporting structure having a thickness therebetween, the supporting structure defining porous flow channels between the minimum surface and the opposite surface, wherein the flow channels have a substantially constant mean diameter from the minimum surface to a point at about one-quarter of the thickness of the supporting structure and an increasing mean diameter from the point to the opposite surface, the membrane having surface pores at the minimum surface of a mean diameter of at least about 1.2 microns and having a lateral transfer rate of greater than about 2 cm per minute; and a sample application area that directs sample first to the opposite surface.

23. The device according to claim 22, wherein the membrane has a bubble point of from about 0.5 psid to about 25 psid.

24. The device according to claim 22, wherein the membrane has a mean aqueous flow rate of from about 4.5 to 25 cm/min psid.

25. In a diagnostic device comprising a lateral wicking means that transfers a sample that is substantially particle free containing an analyte from a sample receiving region of the device to an analyte-detecting region of the device, the improvement comprising:

a lateral wicking means comprising a polymer membrane, the membrane comprising an integral porous skin, lying at one face of the membrane, wherein substantially all of the pores of the skin have diameters greater than about 1.2 microns, and a support region lying below the skin and having an asymmetric structure, the membrane having a lateral transfer rate of greater than about 2 cm per minute; and a sample application area that directs sample first to the opposite surface.

26. The device according to claim 22, wherein the membrane has a bubble point of from about 0.5 psid to about 25 psid.

27. The device according to claim 22, wherein the membrane has a mean aqueous flow rate of from about 4.5 to 25 cm/min psid.

28. In a diagnostic device comprising a lateral wicking means that transfers a sample that is substantially particle free containing an analyte from a sample receiving region of the device to an analyte-detecting region of the device, the improvement comprising:

a lateral wicking means comprising a polymer membrane, the membrane comprising an improved asymmetric polymer membrane having a minimum porous surface, an opposite porous surface, and a porous supporting structure therebetween and having a thickness, the membrane comprising:

a region of generally isotropic structure from the minimum surface to a point at about one-quarter of the thickness of the supporting structure, the membrane having surface pores at the minimum surface of a mean diameter of at least about 1.2 microns and having a lateral transfer rate of greater than about 2 cm per minute; and a sample application area that directs sample first to the opposite surface.

29. The device according to claim 28, wherein the membrane has a bubble point of from about 0.5 psid to about 25 psid.

30. The device according to claim 28, wherein the membrane has a mean aqueous flow rate of from about 4.5 to 25 cm/min psid.

* * * * *